(12) United States Patent
Almirante et al.

(10) Patent No.: US 10,280,138 B2
(45) Date of Patent: May 7, 2019

(54) NITRIC OXIDE DONATING DERIVATIVES OF FLUPROSTENOL

(71) Applicant: NICOX S.A., Sophia Antipolis-Valbonne (FR)

(72) Inventors: Nicoletta Almirante, Milan (IT); Laura Storoni, Cesano Maderno (mb) (IT); Elena Bastia, Milan (IT); Stefania Brambilla, Merone (co) (IT); Francesco Impagnatiello, Milan (IT)

(73) Assignee: NICOX S.A., Sophia Antipolis-Valbonne (FR)

( * ) Notice: Subject to any disclaimer, the term of this patent is extended or adjusted under 35 U.S.C. 154(b) by 0 days.

(21) Appl. No.: 15/561,885

(22) PCT Filed: Jan. 28, 2016

(86) PCT No.: PCT/EP2016/051768
§ 371 (c)(1),
(2) Date: Sep. 26, 2017

(87) PCT Pub. No.: WO2016/155906
PCT Pub. Date: Oct. 6, 2016

(65) Prior Publication Data
US 2018/0118677 A1   May 3, 2018

(30) Foreign Application Priority Data
Mar. 31, 2015 (EP) .................................... 15162000

(51) Int. Cl.
| | | |
|---|---|---|
| *A61K 31/5575* | (2006.01) |
| *A61P 27/06* | (2006.01) |
| *C07D 405/00* | (2006.01) |
| *C07C 405/00* | (2006.01) |

(52) U.S. Cl.
CPC .... *C07C 405/0016* (2013.01); *A61K 31/5575* (2013.01); *A61P 27/06* (2018.01); *C07C 2601/08* (2017.05)

(58) Field of Classification Search
CPC .... A61K 31/5575; A61P 27/06; C07C 405/00
See application file for complete search history.

(56) References Cited

U.S. PATENT DOCUMENTS 5,889,052 A   3/1999   Klimko et al.

FOREIGN PATENT DOCUMENTS

| WO | WO 2005/068421 A1 | 7/2005 |
| WO | WO 2007/000641 A2 | 1/2007 |
| WO | WO 2007/000642 A1 | 1/2007 |
| WO | WO 2009/136281 A1 | 11/2009 |

OTHER PUBLICATIONS

International Search Report and Written Opinion issued in International Application No. PCT/EP2016/051768 dated Feb. 5, 2016.

*Primary Examiner* — Brenda L Coleman
(74) *Attorney, Agent, or Firm* — Arent Fox LLP

(57) ABSTRACT

The present invention relates to 15-nitrooxyderivatives of fluprostenol, their use for the treatment of glaucoma and ocular hypertension and formulation containing 15-nitrooxy derivatives of fluprostenol.

18 Claims, No Drawings

NITRIC OXIDE DONATING DERIVATIVES OF FLUPROSTENOL

CROSS-REFERENCE TO RELATED APPLICATION

This application is a 35 U.S.C. 371 National Phase of PCT Application No. PCT/EP2016/051768 filed Jan. 28, 2016 which claims priority to EP Application No. 15162000.2 filed Mar. 31, 2015. The disclosure of these prior applications are hereby incorporated by reference herein.

The present invention relates to 15-nitrooxyderivatives of fluprostenol, their use for the treatment of glaucoma and ocular hypertension and formulation containing 15-nitrooxy derivatives of fluprostenol.

Glaucoma is a group of eye disorders leading to progressive damage to the optic nerve, and is characterized by loss of nerve tissue resulting in loss of vision. The most common form of glaucoma, primary open-angle glaucoma, is associated with an increase in the fluid pressure inside the eye. This increase in pressure may cause progressive damage to the optic nerve and loss of nerve fibers. Advanced glaucoma may even cause blindness. Glaucoma is the second leading cause of blindness in the U.S. It most often occurs in people over age 40, although a congenital or infantile form of glaucoma exists.

There are many types of glaucoma. The most common form of glaucoma, primary open-angle glaucoma, develops slowly and usually without any symptoms. It initially affects peripheral or side vision, but can advance to central vision loss. If left untreated, glaucoma can lead to significant loss of vision in both eyes, and may even lead to blindness.

A less common type of glaucoma, acute angle closure glaucoma, usually occurs abruptly due to a rapid increase of pressure in the eye.

Secondary glaucoma occurs as a result of an injury or other eye disease. It may be caused by a variety of medical conditions, physical injuries, and eye abnormalities. Infrequently, eye surgery can be associated with secondary glaucoma.

Normal-tension glaucoma, also known as low-tension glaucoma, is characterized by progressive optic nerve damage and visual field loss with normal intra ocular pressure (IOP) and may account for as many as one-third of the cases of open-angle glaucoma in U.S. Normal-tension glaucoma is thought to be, in part, due to poor blood flow to the optic nerve, which leads to death of the ganglion cells which carry impulses from the retina to the brain. A pressure lower than normal is necessary to prevent further visual loss.

The most common first line treatment of glaucoma is drug treatment. Several classes of drugs acting by different mechanisms are used as topically administered ocular therapy to lower IOP. These include beta adrenergic blockers (e.g., timolol), topical carbonic anhydrase inhibitors (e.g., dorzolamide), and alpha 2-adrenergic receptor agonists (e.g., brimonidine), all of which act primarily by decreasing the formation of aqueous humor within the eye. Pilocarpine and epinephrine are clinical agents that also lower IOP in glaucomatous eyes, but these drugs act principally by decreasing the resistance in the trabecular meshwork outflow channels. A third mechanism for lowering IOP in the primate eye is by increasing the outflow of aqueous humor via the uveoscleral route.

Prostaglandin analogs have met an increasing interest for glaucoma therapy as IOP-lowering substances which act primarily by increasing the uveoscleral outflow.

Recently, nitric oxide (NO)-donating prostaglandin derivatives have been studied as IOP-lowering compounds for the treatment of glaucoma and there are some reports on the studies. For example Journal of Ocular Pharmacology and Therapeutics (2010), 26(2), 125-131, Experimental Eye Research (2011), 93(3), 243-249 and Experimental Eye Research (2011), 93(3), 250-255 disclose the IOP lower effect of two NO donating latanoprost acid derivatives. The compound known as BOL-303259-X is now in clinical development for the treatment of primary open-angle glaucoma.

The drug therapies for glaucoma are sometimes associated with significant side effects, for example Timolol and other topically applied beta blockers have been associated with asthma exacerbation, worsening congestive heart failure and, rarely heart block.

Pilocarpine may cause systemic cholinergic effects such as nausea, vomiting, sweating and cutaneous vasodilatation. $PGF_{2\alpha}$ and its esters are characterized by the occurrence of ocular side effects, primarily conjunctival hyperemia.

Patients with glaucoma need to continue treatment for the rest of their lives. Because the disease can progress, only by keeping eye pressure under control can continued damage to the optic nerve and continued loss of visual field be slowed or stopped.

Intraocular pressure is the primary risk factor for glaucoma and lowering IOP to prevent optic nerve injury is the only proven effective treatment (Kass M A, et al., Arch Ophthalmol, 2002, 120:701-703; The AGIS Investigators, Am J Ophthalmol, 2000, 130:429-440).

U.S. Pat. No. 5,889,052 discloses that fluprostenol analogues are useful in lowering intraocular pressure and thus are useful in the treatment of glaucoma. According to U.S. Pat. No. 5,889,052, fluprostenol analogues include 15-alky esters and 15-alkyl ethers of fluprostenol isopropyl ester.

PCT publications WO 2005/068421, WO 2009/136281, WO 2007/000641 and WO 2007/0642 describe (NO)-donating prostaglandin derivatives with increased ocular hypotensive activity in particular WO 2009/136281 discloses 15-nitrooxyderivative of prostamides such as bimatoprost. Said compounds have been shown to have greater hypotensive efficacy than the parent compound.

In spite of all the treatments evolved over decades as described above, there is still a need for new drugs for treatments and therapies for glaucoma and elevated intra ocular pressure.

Thus, this invention provides 15-nitrooxyderivatives of fluprostenol useful for the treatment of glaucoma and elevated intraocular pressure.

It has now been found that 15-nitrooxyderivatives of fluprostenol are efficacious and potent ocular hypotensive agents and therefore the 15-nitrooxyderivatives of fluprostenol of the present invention can be employed for treating ocular hypertension and glaucoma, in particular chronic open-angle glaucoma.

An embodiment of the invention relates to compounds of formula (I) or salts thereof

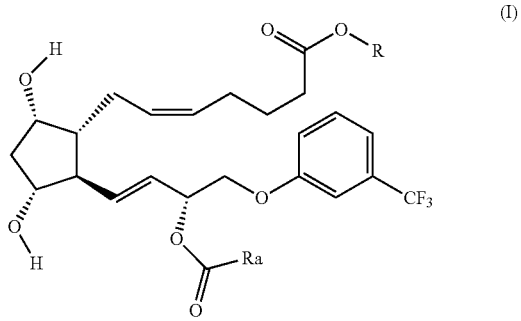

(I)

wherein

R is —CH(CH$_3$)$_2$ or H; preferably R is —CH(CH$_3$)$_2$;

Ra is selected from

A1): —(CHR$^1$)—NH—(C=O)—(CH$_2$)$_m$—[O—(CH$_2$)$_n$]$_p$—(CH—ONO$_2$)$_q$—CH$_2$—ONO$_2$

A2): —(CH$_2$)$_2$—NH—(C=O)—(CH$_2$)$_m$—[O—(CH$_2$)$_n$]$_p$—(CH—ONO$_2$)$_q$—CH$_2$—ONO$_2$

A3): —(CH$_2$)$_m$—[O—(CH$_2$)$_n$]$_p$—(CH—ONO$_2$)$_q$—CH$_2$—ONO$_2$ wherein

R$^1$ is —H or —CH$_3$, p is 1 or 0, q is 1 or 0, m is an integer ranging from 1 to 10; preferably m is from 1 to 6;

n is an integer ranging from 1 to 6; preferably n is 1 or 2;

preferably Ra is selected from A1) and A3).

Preferred linkers having structure A1 are below reported:

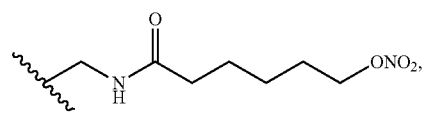
(1-A1)

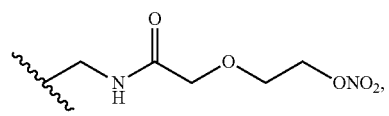
(2-A1)

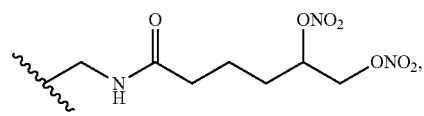
(3-A1)

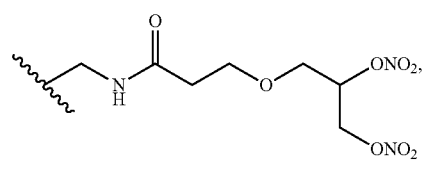
(4-A1)

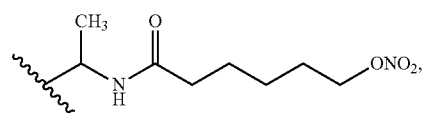
(5-A1)

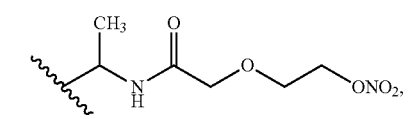
(6-A1)

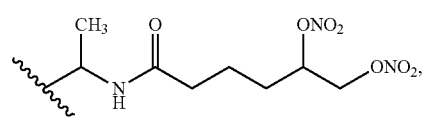
(7-A1)

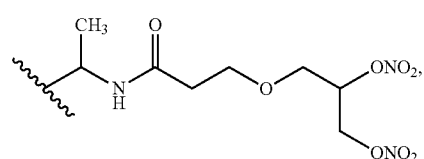
(8-A1)

preferred linkers having structure A2 are below reported:

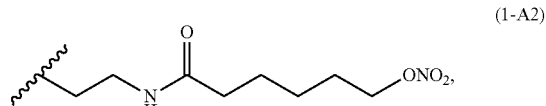
(1-A2)

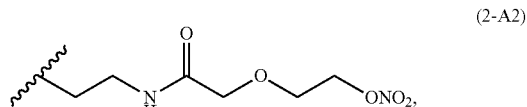
(2-A2)

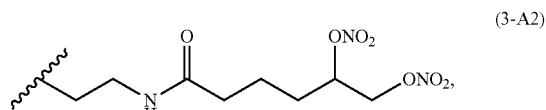
(3-A2)

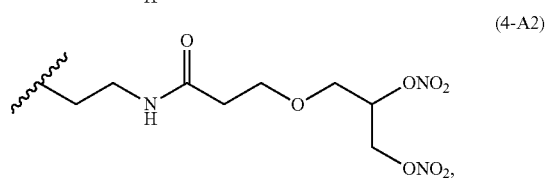
(4-A2)

preferred linkers having structure of the group A3 are below reported:

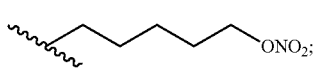
(1-A3)

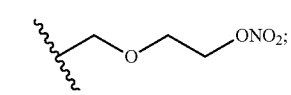
(2-A3)

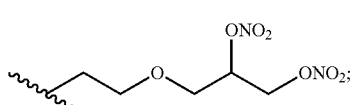
(3-A3)

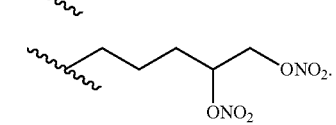
(4-A3)

Another embodiment of the invention relates to compounds of formula (I) as above defined or a salt thereof wherein R is —CH(CH$_3$)$_2$;

Ra is A1): —(CHR$^1$)—NH—(C=O)—(CH$_2$)$_m$—[O—(CH$_2$)$_n$]$_p$—(CH—ONO$_2$)$_q$—CH$_2$—ONO$_2$ wherein R$^1$ is —H or —CH$_3$, p is 1 or 0, q is 1 or 0, m is an integer ranging from 1 to 10; preferably m is from 1 to 6;

n is an integer ranging from 1 to 6; preferably n is 1 or 2.

Another embodiment of the invention relates to compounds of formula (I) as above defined wherein R is —CH(CH$_3$)$_2$ and Ra is selected from the following group of linkers having structure A1:

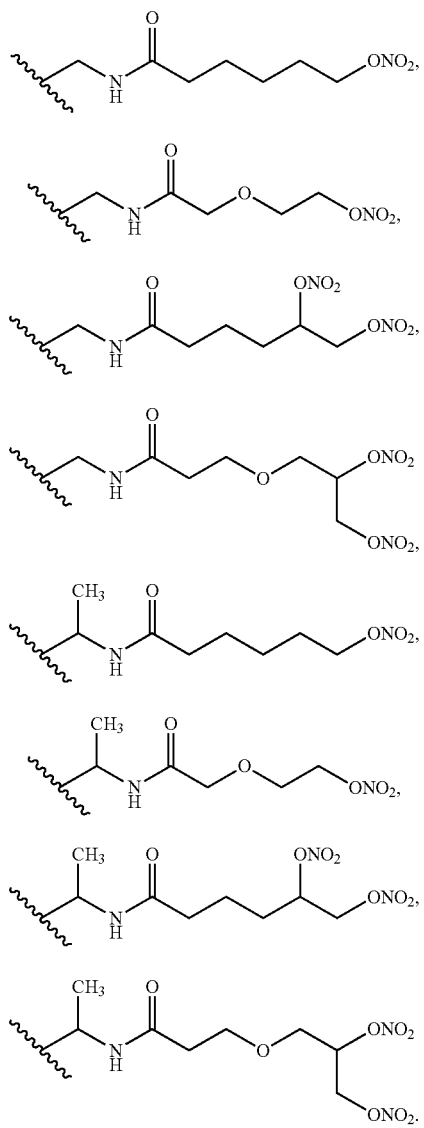

(1-A1)
(2-A1)
(3-A1)
(4-A1)
(5-A1)
(6-A1)
(7-A1)
(8-A1)

An embodiment of the invention relates to compounds of formula (I) as above defined or a salt thereof wherein R is —CH(CH$_3$)$_2$;

Ra is A2): —(CH$_2$)$_2$—NH—(C=O)—(CH$_2$)$_m$—[O—(CH$_2$)$_n$]$_p$—(CH—ONO$_2$)$_q$—CH$_2$—ONO$_2$ wherein p is 1 or 0, q is 1 or 0, m is an integer ranging from 1 to 10; preferably m is from 1 to 6;

n is an integer ranging from 1 to 6; preferably n is 1 or 2.

An embodiment of the invention relates to compounds of formula (I) as above defined wherein R is —CH(CH$_3$)$_2$ and Ra is selected from the following group of linkers having structure A2:

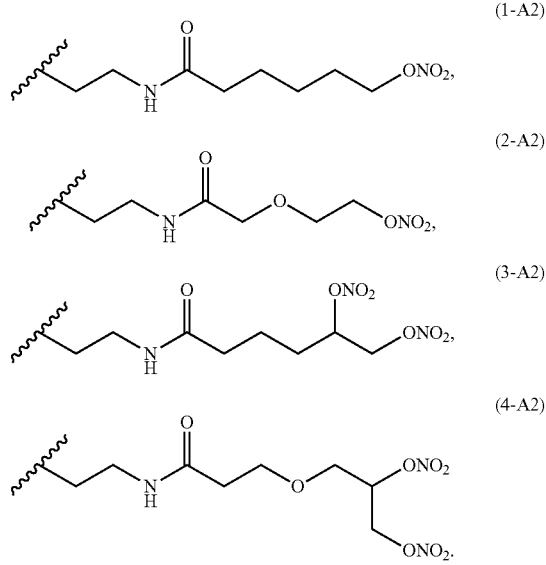

(1-A2)
(2-A2)
(3-A2)
(4-A2)

An embodiment of the invention relates to compounds of formula (I) as above defined or a salt thereof wherein R is —CH(CH$_3$)$_2$;

Ra is A3): —(CH$_2$)$_m$—[O—(CH$_2$)$_n$]$_p$—(CH—ONO$_2$)$_q$—CH$_2$—ONO$_2$ wherein p is 1 or 0, q is 1 or 0, m is an integer ranging from 1 to 10; preferably m is from 1 to 6;

n is an integer ranging from 1 to 6; preferably n is 1 or 2.

An embodiment of the invention relates to compounds of formula (I) as above defined wherein R is —CH(CH$_3$)$_2$ and Ra is selected from the following group of linkers having structure A3:

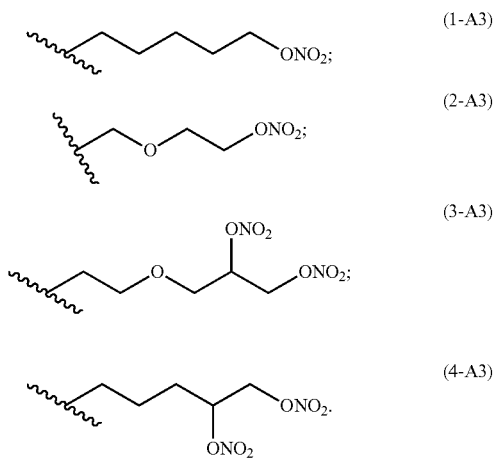

(1-A3)
(2-A3)
(3-A3)
(4-A3)

Another embodiment of the invention relates to compounds of formula (I) as above defined or salts thereof wherein R is —H;

Ra is A1): —(CHR$^1$)—NH—(C=O)—(CH$_2$)$_m$—[O—(CH$_2$)$_n$]$_p$—(CH—ONO$_2$)$_q$—CH$_2$—ONO$_2$ wherein R$^1$ is —H or —CH$_3$, p is 1 or 0, q is 1 or 0, m is an integer ranging from 1 to 10; preferably m is from 1 to 6;

n is an integer ranging from 1 to 6; preferably n is 1 or 2.

Another embodiment of the invention relates to compounds of formula (I) as above defined wherein R is —H and Ra is selected from the following group of linkers having structure A1:

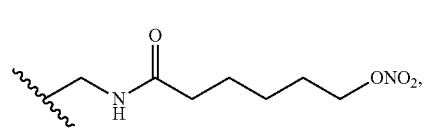
(1-A1)

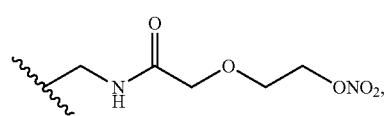
(2-A1)

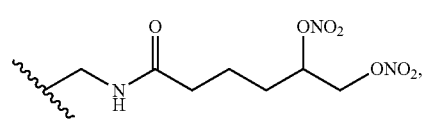
(3-A1)

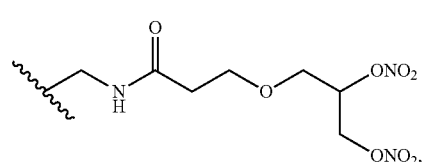
(4-A1)

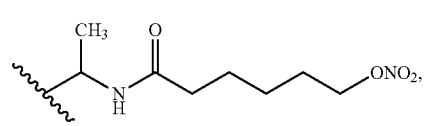
(5-A1)

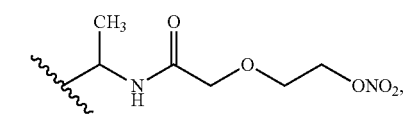
(6-A1)

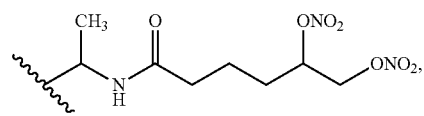
(7-A1)

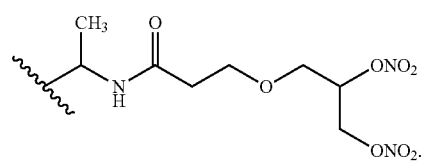
(8-A1)

An embodiment of the invention relates to compounds of formula (I) as above defined or salts thereof wherein R is —H;

Ra is A2): —(CH$_2$)$_2$—NH—(C=O)—(CH$_2$)$_m$—[O—(CH$_2$)$_n$]$_p$—(CH—ONO$_2$)$_q$—CH$_2$—ONO$_2$ wherein p is 1 or 0, q is 1 or 0, m is an integer ranging from 1 to 10; preferably m is from 1 to 6;

n is an integer ranging from 1 to 6; preferably n is 1 or 2.

An embodiment of the invention relates to compounds of formula (I) as above defined wherein R is —H and Ra is selected from the following group of linkers having structure A2:

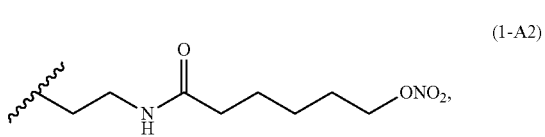
(1-A2)

(2-A2)

(3-A2)

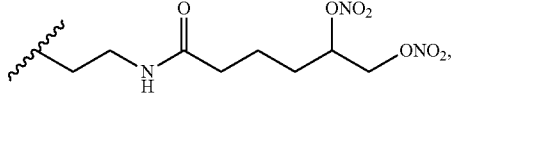
(4-A2)

An embodiment of the invention relates to compounds of formula (I) as above defined or salts thereof wherein R is —H;

Ra is A3): —(CH$_2$)$_m$[O—(CH$_2$)$_n$]$_p$—(CH—ONO$_2$)$_q$—CH$_2$—ONO$_2$ wherein p is 1 or 0, q is 1 or 0, m is an integer ranging from 1 to 10; preferably m is from 1 to 6;

n is an integer ranging from 1 to 6; preferably n is 1 or 2.

An embodiment of the invention relates to compounds of formula (I) as above defined wherein R is —H and Ra is selected from the following group of linkers having structure A3:

(Z)-isopropyl 7-((1R,2R,3R,5S)-2-((3R,E)-3-(3-(5,6-bis (nitrooxy)hexanamido) propanoyloxy)-4-(3-(trifluoromethyl)phenoxy)but-1-enyl)-3,5-dihydroxycyclopentyl) hept-5-enoate (Compound (2))

Another embodiment of the inventions relates to a compound of formula (I) selected from the following group of compounds:

(Z)-isopropyl 7-((1R,2R,3R,5S)-3,5-dihydroxy-2-((R,E)-3-(3-(6-(nitrooxy) hexanamido) propanoyloxy)-4-(3-(trifluoromethyl)phenoxy)but-1-enyl)cyclopentyl)hept-5-enoate (Compound (1))

(Z)-isopropyl 7-((1R,2R,3R,5S)-3,5-dihydroxy-2-((R,E)-3-(3-(2-(2-(nitrooxy) ethoxy)acetamido)propanoyloxy)-4-(3-(trifluoromethyl)phenoxy)but-1-enyl)cyclopentyl) hept-5-enoate (Compound (3))

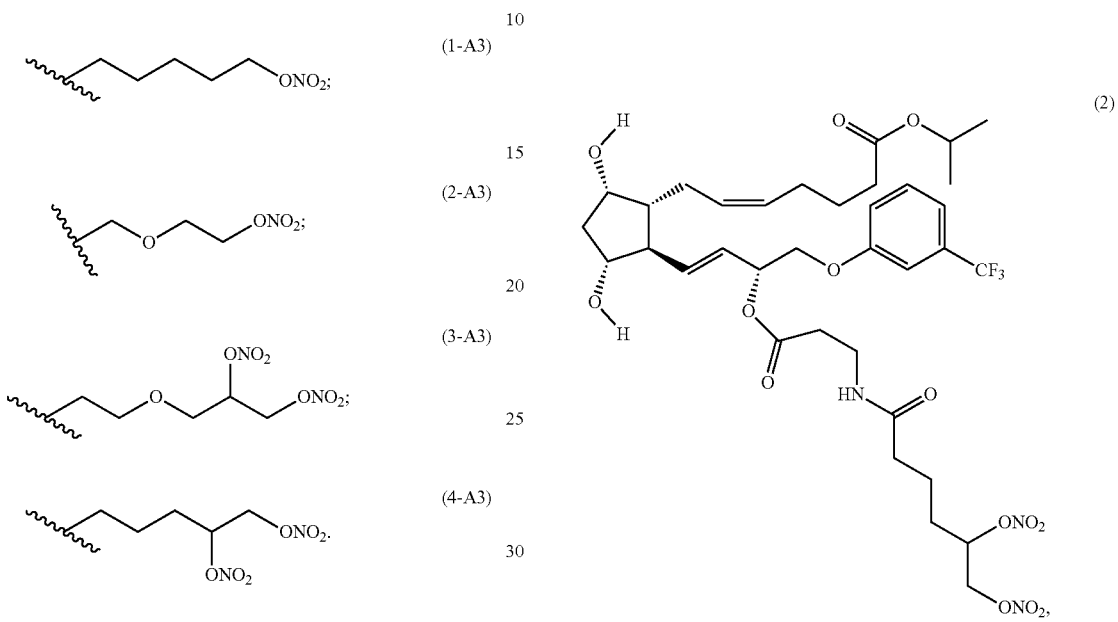

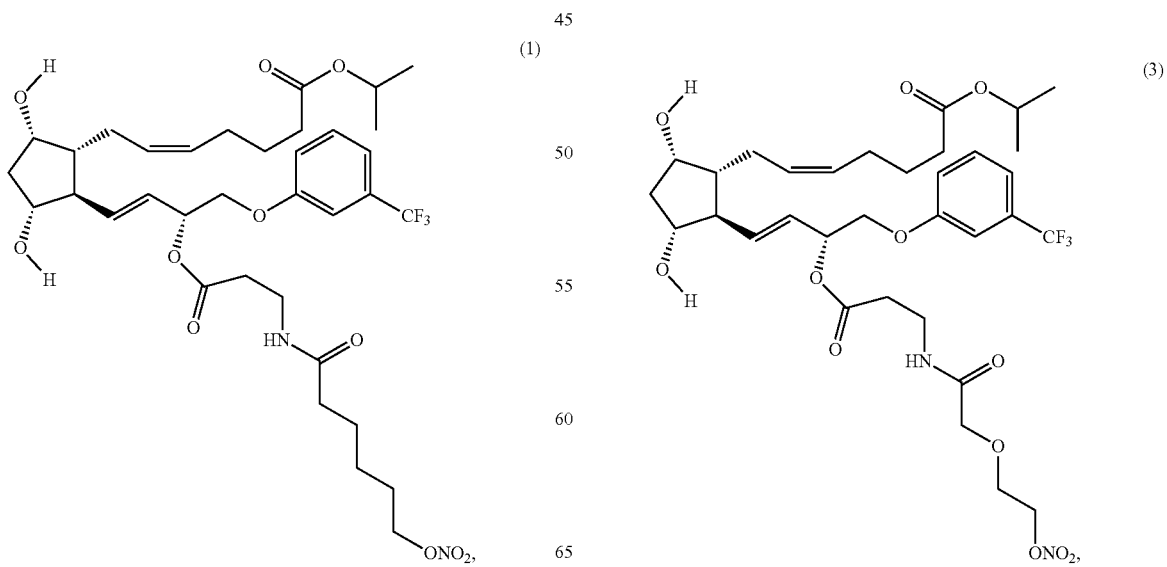

(Z)-isopropyl 7-((1R,2R,3R,5S)-2-((3R,E)-3-(3-(3-(2,3-bis(nitrooxy)propoxy) propanamido)propanoyloxy)-4-(3-(trifluoromethyl)phenoxy)but-1-enyl)-3,5-dihydroxycyclopentyl)hept-5-enoate (Compound (4))

(Z)-isopropyl 7-((1R,2R,3R,5S)-2-((3R,E)-3-(2-(5,6-bis(nitrooxy)hexanamido) acetoxy)-4-(3-(trifluoromethyl)phenoxy)but-1-enyl)-3,5-dihydroxycyclopentyl)hept-5-enoate (Compound (6))

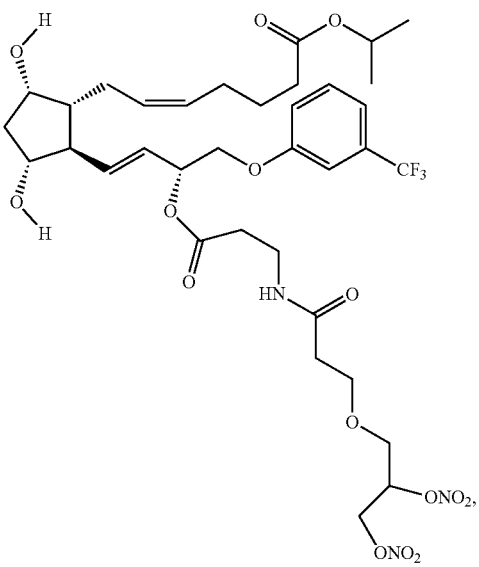

(4)

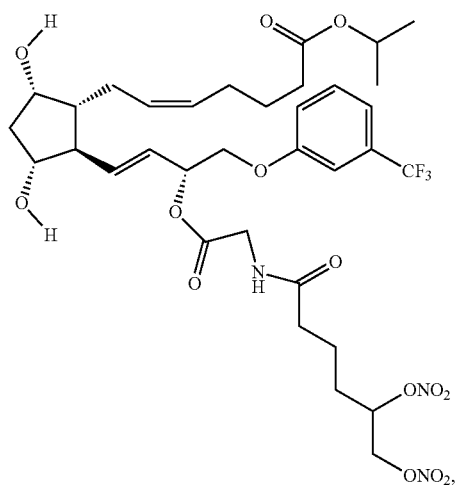

(6)

(Z)-isopropyl 7-((1R,2R,3R,5S)-3,5-dihydroxy-2-((R,E)-3-(2-(6-(nitrooxy) hexanamido)acetoxy)-4-(3-(trifluoromethyl)phenoxy)but-1-enyl)cyclopentyl)hept-5-enoate (Compound (5))

(Z)-isopropyl 7-((1R,2R,3R,5S)-3,5-dihydroxy-2-((R,E)-3-(2-(2-(2-(nitrooxy)ethoxy)acetamido)acetoxy)-4-(3-(trifluoromethyl)phenoxy)but-1-enyl) cyclopentyl)hept-5-enoate (Compound (7))

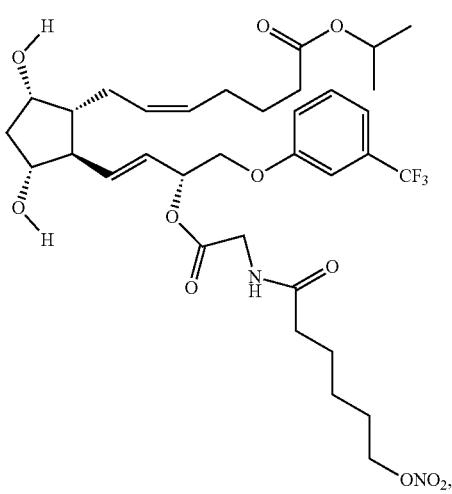

(5)

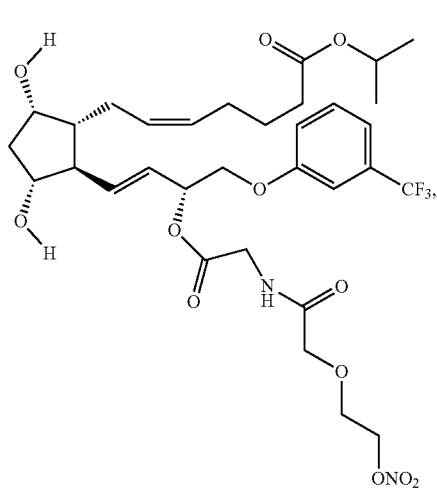

(7)

(Z)-isopropyl 7-((1R,2R,3R,5S)-2-((3R,E)-3-(2-(3-(2,3-bis(nitrooxy)propoxy) propanamido)acetoxy)-4-(3-(trifluoromethyl)phenoxy)but-1-enyl)-3,5-dihydroxycyclopentyl)hept-5-enoate (Compound (8))

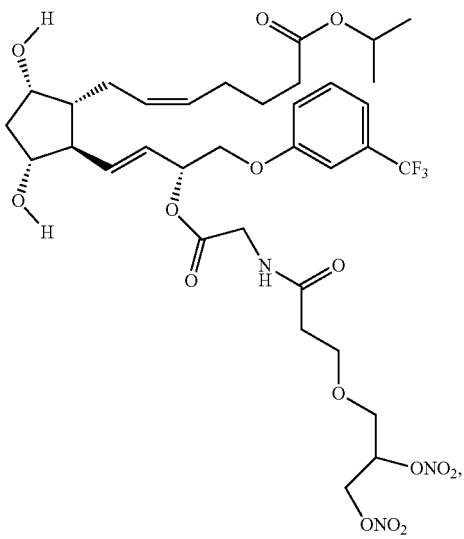

(Z)-isopropyl 7-((1R,2R,3R,5S)-3,5-dihydroxy-2-4R,E)-3-(6-(nitrooxy)hexanoyloxy)-4-(3-(trifluoromethyl)phenoxy)but-1-enyl)cyclopentyl)hept-5-enoate (Compound (9))

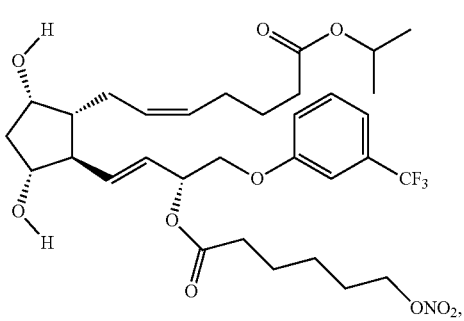

(Z)-isopropyl 7-((1R,2R,3R,5S)-2-((3R,E)-3-(5,6-bis(nitrooxy)hexanoyloxy)-4-(3-(trifluoromethyl)phenoxy)but-1-enyl)-3,5-dihydroxycyclopentyl)hept-5-enoate (Compound (10))

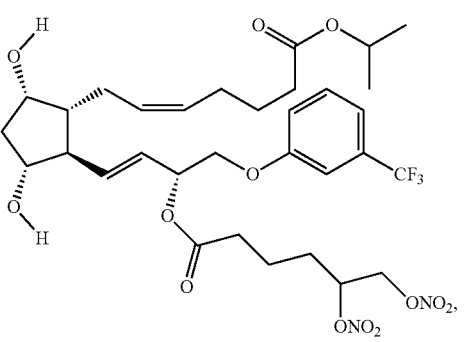

(Z)-isopropyl 7-((1R,2R,3R,5S)-3,5-dihydroxy-2-((R,E)-3-(2-(2-nitrooxyethoxy) acetoxy)-4-(3-(trifluoromethyl)phenoxy)but-1-enyl)cyclopentyl)hept-5-enoate (Compound (11))

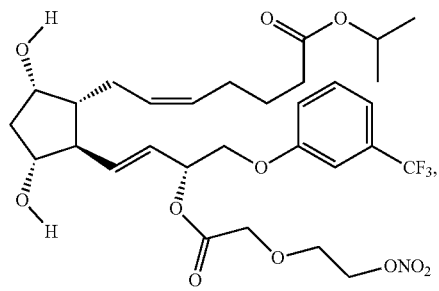

(Z)-isopropyl 7-((1R,2R,3R,5S)-2-((3R,E)-3-(3-(2,3-bis(nitrooxy)propoxy) propanoyl oxy)-4-(3-(trifluoromethyl)phenoxy)but-1-enyl)-3,5 dihydroxycyclopentyl)hept-5-enoate (Compound (12))

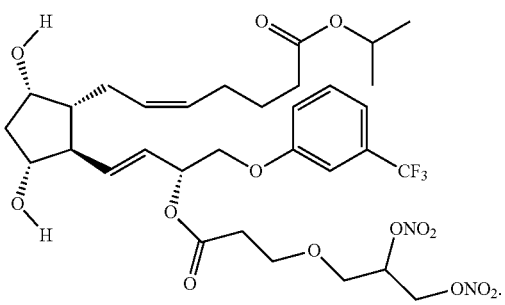

(Z)-7-((1R,2R,3R,5S)-2-((R,E)-3-(5,6-bis(nitrooxy)hexanoyloxy)-4-(3-(trifluoromethyl)phenoxy)but-1-enyl)-3,5-dihydroxycyclopentyl)hept-5-enoic acid (Compound (13))

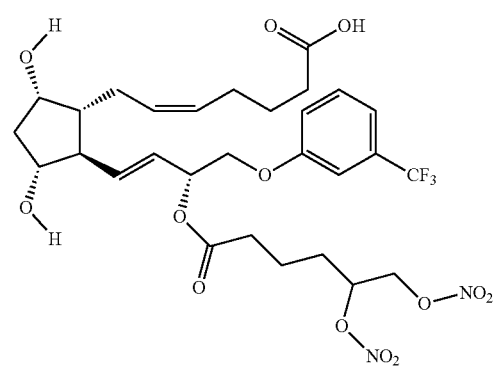

The 15-nitrooxyderivatives of fluprostenol isopropyl ester have an improved IOP-reducing efficacy as compared to the known nitrooxyderivatives of prostaglandin analogues.

The term "salt" has the meaning normally understood by those of ordinary skill in the art. Pharmaceutically acceptable salts of acidic functional groups may be related to organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines.

Included within the scope of the present invention are the individual enantiomers of the compounds of formula (I), as well as their racemic and non-racemic mixtures.

Another embodiment provides the use of compound of formula (I) for treating ocular hypertension.

Another embodiment provides the use of compound of formula (I) for treating glaucoma in particular primary open angle glaucoma, normal intraocular tension glaucoma, pseudoexfoliation glaucoma, acute angle-closure glaucoma, chronic closed angle glaucoma.

The compound may be provided as part of a pharmaceutical composition as described therein.

In forming the compositions for topical administration, the compounds of the present invention are generally formulated as between about 0.00003 to about 3 percent by weight (wt %) solutions in water at a pH between 4.5 to 8.0. The compounds are preferably formulated as between about 0.003 to about 1 wt % and, most preferably, between about 0.004 and about 0.3 wt %.

In another aspect, there is provided a topical ocular pharmaceutical composition. The pharmaceutical composition includes a compound of formula (I) or salts thereof and a pharmaceutically acceptable excipient. Acceptable excipients may include preservatives, dissolving agents and viscosity agents.

Suitable preservatives include: benzalkonium chloride, thimerosal, chlorobutanol, methyl paraben, propyl paraben, phenylethyl alcohol, edetate disodium, sorbic acid or other agents known to those skilled in the art. Such preservatives are typically employed at a concentration between about 0.001% and about 1.0% by weight. Dissolving agents include: polysorbates for example polyoxyethylene sorbitan monolaurate, and polyoxyethylene sorbitan monooleate for polysorbate 80, polyoxylated castor oil such as polyoxyethylene hydrogenated castor oil 40 and polyoxyethylene hydrogenated castor oil 60, polyoxyl stearate, macrogol, propylene glycol; or other agents known to those skilled in the art. The dissolving agent may be used solely or in combination with one or more other dissolving agents.

Viscosity agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art.

The ophthalmic composition of the present invention may further contain other additives. Examples of the additives may include osmotic adjusting agents such as sodium chloride, potassium chloride, calcium chloride, sodium bicarbonate, sodium carbonate, magnesium sulfate, sodium hydrogen phosphate, sodium dihydrogen phosphate, dipotassium hydrogen phosphate, borax, sodium hydroxide, hydrochloric acid, isosorbitol, propylene glycol, mannitol, sucrose and glucose; buffering agents such as sodium monohydrogen phosphate and sodium dihydrogen phosphate.

The compound of the present invention can also be used in combination with the following classes of drugs: Beta-adrenergic antagonists including carteolol, levobunolol, metipranolol, timolol hemihydrate; Adrenergic agonists including non-selective adrenergic agonists such as epinephrine borate, epinephrine hydrochloride, and dipivefrin; and Alpha2-selective adrenergic agonists such as apraclonidine and the like; Carbonic Anhydrase Inhibitors including such as acetazolamide, dichlorphenamide, methazolamide, brinzolamide, dorzolamide; Cholinergic agonists such as carbachol, pilocarpine hydrochloride, pilocarbine nitrate, pilocarpine; Cholinesterase inhibitors such as demecarium, echothiophate, physostigmine.

Another embodiment of the invention relates to a composition comprising a compound of formula (I) and at least another active agent selected from the following classes of drugs: Beta-adrenergic antagonists including carteolol, levobunolol, metipranolol, timolol hemihydrate; Adrenergic agonists including non-selective adrenergic agonists such as epinephrine borate, epinephrine hydrochloride, and dipivefrin; and Alpha2-selective adrenergic agonists such as apraclonidine and the like; Carbonic Anhydrase Inhibitors including such as acetazolamide, dichlorphenamide, methazolamide, brinzolamide, dorzolamide; Cholinergic agonists such as carbachol, pilocarpine hydrochloride, pilocarbine nitrate, pilocarpine; Cholinesterase inhibitors such as demecarium, echothiophate, physostigmine.

General Synthesis

1) The compound of formula (I) wherein R is —CH(CH$_3$)$_2$ and Ra is selected from the groups A1), A2) or A3):

A1): —(CHR$^1$)—NH—(C=O)—(CH$_2$)$_m$—[O—(CH$_2$)$_n$]$_p$—(CH—ONO$_2$)$_q$—CH$_2$—ONO$_2$

A2): —(CH$_2$)$_2$—NH—(C=O)—(CH$_2$)$_m$—[O—(CH$_2$)$_n$]$_p$—(CH—ONO$_2$)$_q$—CH$_2$—ONO$_2$

A3): —(CH$_2$)$_m$—[O—(CH$_2$)$_p$]$_p$—(CH—ONO$_2$)$_q$—CH$_2$—ONO$_2$ wherein:

R$^1$, m, n, p and q are as above defined;

can be prepared by reacting a compound of formula (II), wherein A is as above defined, with methanol or other alcohols:

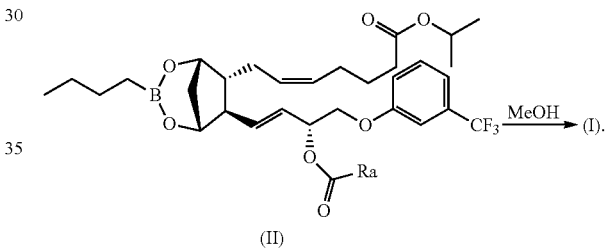

(II)

Compounds of formula (II), wherein Ra is as above defined, can be generally prepared by reacting a compound of formula (III) with compounds of formula (IVa-c):

(IVa) =HOOC—(CHR$^1$)—NH—(C=O)—(CH$_2$)$_m$—[O—(CH$_2$)$_n$]$_p$—(CH—ONO$_2$)$_q$—CH$_2$—ONO$_2$ (IVb) =HOOC—(CH$_2$)$_2$—NH—(C=O)—(CH$_2$)$_m$—[O—(CH$_2$)$_n$]$_p$—(CH—ONO$_2$)$_q$—CH$_2$—ONO$_2$ (IVC) =HOOC—(CH$_2$)$_m$—[O—(CH$_2$)$_n$]$_p$—(CH—ONO$_2$)$_q$—CH$_2$—ONO$_2$ as depicted in the below reported scheme:

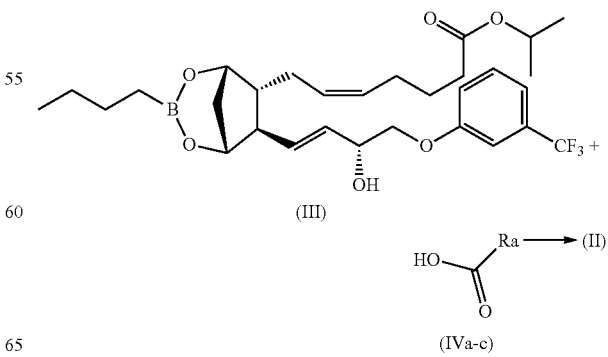

The reaction is carried out in a aprotic polar/non polar solvent such as THF, DMF or $CH_2Cl_2$, in presence of DCC, EDAC, HBTU, HATU or other coupling reagents, in presence of catalytic amount of DMAP at temperature ranging from $-0°$ C. to $80°$ C.

Alternatively, the compounds of formula (II) can be generally prepared by reacting a compound of formula (III) with compounds of formula (Va-c):

(Va) =XOC—(CH$_1$V)—NH—(C=O)—(CH$_2$)$_m$—[O—(CH$_2$)$_n$]$_p$—(CH—ONO$_2$)$_q$—CH$_2$—ONO$_2$ (Vb) =XOC—(CH$_2$)$_2$—NH—(C=O)—(CH$_2$)$_m$—[O—(CH$_2$)$_n$]$_p$—(CH—ONO$_2$)$_q$—CH$_2$—ONO$_2$ (Vc) =XOC—(CH$_2$)$_m$—[O—(CH$_2$)$_n$]$_p$—(CH—ONO$_2$)$_q$—CH$_2$—ONO$_2$ wherein X is —Cl, p-nitrophenoxy, pentafluorophenoxy or 2,5-pyrrolidinedione, 1-oxy, as depicted in the below reported scheme:

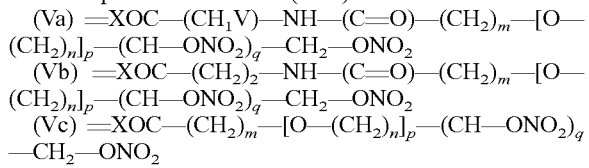
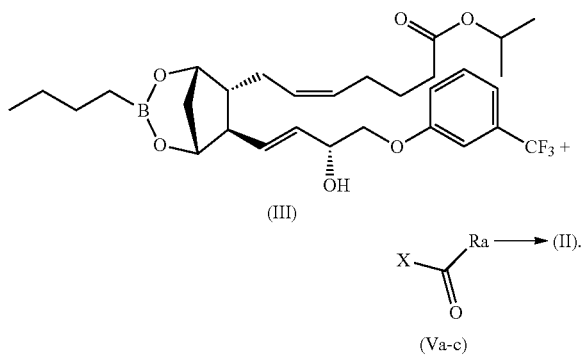
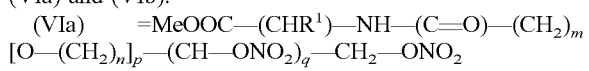

When X=—Cl, the reaction is carried out in presence of a base such as DMAP, pyridine or triethylamine or $K_2CO_3$, $Cs_2CO_3$ in an aprotic/non polar solvent such as THF, DMF or $CH_2Cl_2$, at a temperature ranging from $-20°$ C. to $60°$ C.

When X is selected from p-nitrophenoxy, pentafluorophenoxy or 2,5-pyrrolidinedione, 1-oxy, the reaction is carried out in a aprotic polar/non polar solvent such as THF, DMF or $CH_2Cl_2$, in presence of DMAP at temperature ranging from $0°$ C. to $80°$ C.

The compound of formula (III) is known in the literature and can be prepared, by reacting the isopropyl ester of fluprostenol with butylboronic acid following a general procedure reported in Organic Syntheses, Coll. Vol. 10, p. 613 (2004).

Compounds of formula (IVa) and (IVb) can be prepared by basic hydrolysis of correspondent compounds of (VIa) and (VIb):

(VIa) =MeOOC—(CHR$^1$)—NH—(C=O)—(CH$_2$)$_m$[O—(CH$_2$)$_n$]$_p$—(CH—ONO$_2$)$_q$—CH$_2$—ONO$_2$ (VIb) =MeOOC—(CH$_2$)$_2$—NH—(C=O)—(CH$_2$)$_m$[O—(CH$_2$)$_n$]$_p$—(CH—ONO$_2$)$_q$—CH$_2$—ONO$_2$ wherein R$^1$, m, n, p, q are as above defined.

Compounds of formula (VIa) and (VIb) can be prepared by reacting compounds (IVc) or (Vc) with commercially available compounds of formula (VIIa) or (VIIb):

(VIIa) =MeOOC—(CHR$^1$)—NH$_2$ (VIIb) =MeOOC—(CH$_2$)$_2$—NH$_2$ wherein R' is as above defined, according to methods well known in the art.

Alternatively compounds of formula (IVa) and (IVb) can be prepared by acid hydrolysis of correspondent compounds of formula (VIc) and (VId):

(VIc) =t-ButOOC—(CHR$^1$)—NH—(C=O)—(CH$_2$)$_m$—[O—(CH$_2$)$_n$]$_p$—(CH—ONO$_2$)$_q$—CH$_2$—ONO$_2$ (VId) =t-ButOOC—(CH$_2$)$_2$—NH—(C=O)—(CH$_2$)$_m$—[O—(CH$_2$)$_n$]$_p$—(CH—ONO$_2$)$_q$—CH$_2$—ONO$_2$ wherein R$^1$, m, n, p, q are as above defined.

Compounds of formula (VIc) and (VId) can be prepared by reacting compounds (IVc) or (Vc) with commercially available compounds of formula (VIIc) or (VIId):

(VIIc) =t-ButOOC—(CHR$^1$)—NH$_2$ (VIId) =t-ButOOC—(CH$_2$)$_2$—NH$_2$ wherein R$^1$ is as above defined, according to methods well known in the art.

Compounds (IVc) are known in the art or can be prepared from known compounds by known methods such as for example from the corresponding alcohols of formula (VIIIa), (VIIIa) =HO—CH$_2$—(CH$_2$)$_m$—[O—(CH$_2$)$_n$]$_p$—(CH—ONO$_2$)$_q$—CH$_2$—ONO$_2$ wherein m, n, p and q are as above defined, by oxidation with known agents such as TEMPO or Ruthenium (IV) oxide/Sodium periodate.

2) The compound of formula (I) wherein R is —H and Ra is selected from the groups A1), A2) or A3):

A1): —(CHR$^1$)—NH—(C=O)—(CH$_2$)$_m$—[O—(CH$_2$)$_n$]$_p$—(CH—ONO$_2$)$_q$—CH$_2$—ONO$_2$

A2): —(CH$_2$)$_2$—NH—(C=O)—(CH$_2$)$_m$—[O—(CH$_2$)$_n$]$_p$—(CH—ONO$_2$)$_q$—CH$_2$—ONO$_2$

A3): —(CH$_2$)$_m$—[O—(CH$_2$)$_n$]$_p$—(CH—ONO$_2$)$_q$—CH$_2$—ONO$_2$ wherein:

R$^1$, m, n, p and q are as above defined;

can be prepared by deprotecting an allyl or isoprenyl ester of formula (IX), wherein Ra is as above defined and Y is —H or —CH$_3$, with methods known in the literature (see for example: T. W. Greene, P. G. M. Wuts "Protective groups in organic Synthesis", 4th edition, J. Wiley & Sons, New York, 2006) and eventually reacting the deprotected compound in MeOH as already described for compound (II):

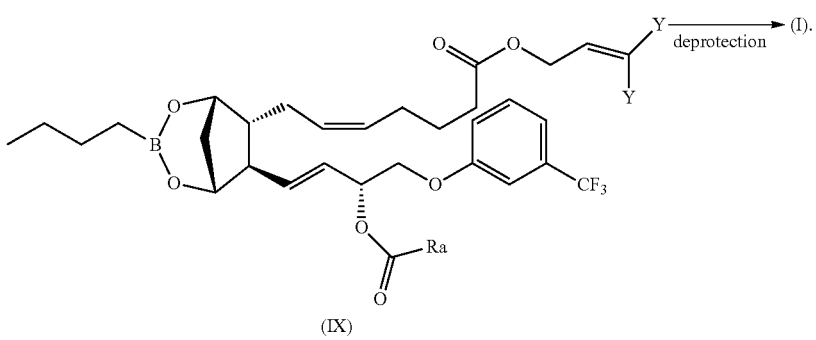

Compounds of formula (IX), wherein Ra is as above defined, can be generally prepared by reacting a compound of formula (X) with compounds of formula (IVa-c):

(IVa)  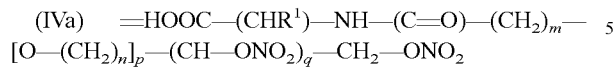
=HOOC—(CHR¹)—NH—(C=O)—(CH₂)ₘ—[O—(CH₂)ₙ]ₚ—(CH—ONO₂)q—CH₂—ONO₂

(IVb)  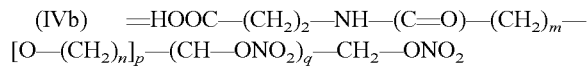
=HOOC—(CH₂)₂—NH—(C=O)—(CH₂)ₘ—[O—(CH₂)ₙ]ₚ—(CH—ONO₂)q—CH₂—ONO₂

(IVC)  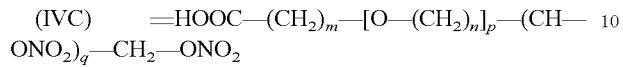
=HOOC—(CH₂)ₘ—[O—(CH₂)ₙ]ₚ—(CH—ONO₂)q—CH₂—ONO₂ as depicted in the below reported scheme;

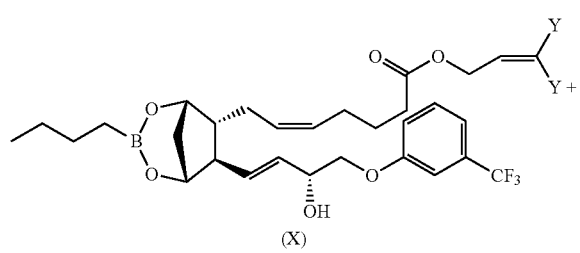
(X)

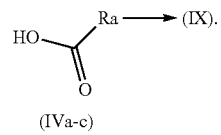
(IVa-c)

The reaction is carried out in a aprotic polar/non polar solvent such as THF, DMF or CH₂Cl₂, in presence of DCC, EDAC, HBTU, HATU or other coupling reagents, in presence of catalytic amount of DMAP at temperature ranging from 0° C. to 80° C.

Alternatively, the compounds of formula (IX) can be generally prepared by reacting a compound of formula (X) with compounds of formula (Va-c):

(Va)  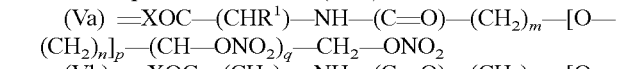
=XOC—(CHR¹)—NH—(C=O)—(CH₂)ₘ—[O—(CH₂)ₙ]ₚ—(CH—ONO₂)q—CH₂—ONO₂

(Vb)  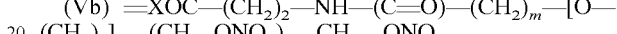
=XOC—(CH₂)₂—NH—(C=O)—(CH₂)ₘ—[O—(CH₂)ₙ]ₚ—(CH—ONO₂)q—CH₂—ONO₂

(Vc)  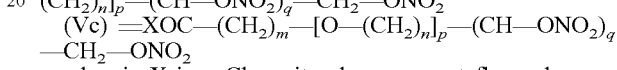
=XOC—(CH₂)ₘ—[O—(CH₂)ₙ]ₚ—(CH—ONO₂)q—CH₂—ONO₂ wherein X is —Cl, p-nitrophenoxy, pentafluorophenoxy or 2,5-pyrrolidinedione, 1-oxy as depicted in the below reported scheme:

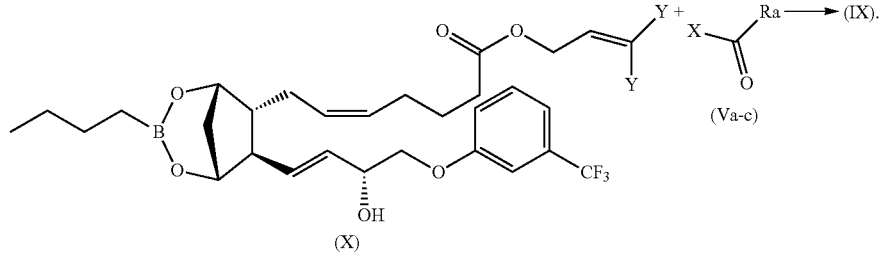

When X=—Cl, the reaction is carried out in presence of a base such as DMAP, pyridine or triethylamine or K₂CO₃, Cs₂CO₃ in an aprotic/non polar solvent such as THF, DMF or CH₂Cl₂, at a temperature ranging from −20° C. to 60° C.

When X is selected from p-nitrophenoxy, pentafluorophenoxy or 2,5-pyrrolidinedione, 1-oxy, the reaction is carried out in a aprotic polar/non polar solvent such as THF, DMF or CH₂Cl₂, in presence of DMAP at temperature ranging from 0° C. to 80° C.

The compound of formula (X) can be prepared as already described for analogous compound (III) by reacting a compound (XI) with butylboronic acid following a general procedure reported in Organic Syntheses, Coll. Vol. 10, p. 613 (2004).

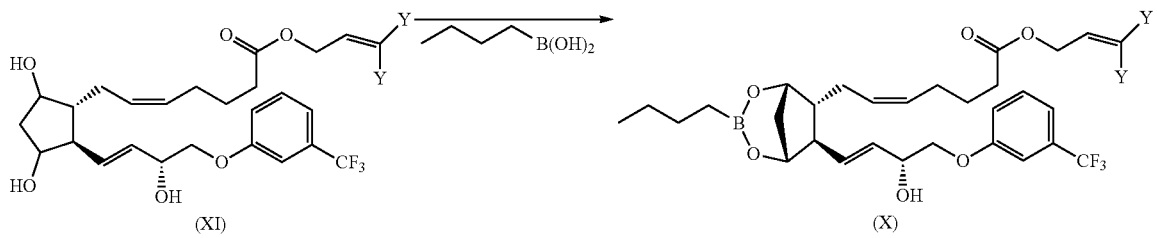

Compound (XI) can be prepared from fluprostenol by known methods, as by reacting fluprostenol with allyl chloride (Y=H) or 2-Butene, 1-chloro-3-methyl-(Y=CH₃) in the presence of an organic or inorganic base following general procedures known in the literature (see for example: T. W. Greene, P. G. M. Wuts "Protective groups in organic Synthesis", 4th edition, J. Wiley & Sons, New York, 2006).

Alternatively the compound of formula (I) wherein R is —H and Ra is selected from the groups A1), A2) or A3):

A1): —(CHR¹)—NH—(C=O)—(CH₂)$_m$—[O—(CH₂)$_n$]$_p$—(CH—ONO₂)$_q$—CH₂—ONO₂

A2): —(CH₂)₂—NH—(C=O)—(CH₂)$_m$—[O—(CH₂)$_n$]$_p$—(CH—ONO₂)$_q$—CH₂—ONO₂

A3): —(CH₂)$_m$—[O—(CH₂)$_n$]$_p$—(CH—ONO₂)$_q$—CH₂—ONO₂ wherein:

R¹, m, n, p and q are as above defined;

can be prepared by reacting compound (XII) with MeOH as already described for compound (II):

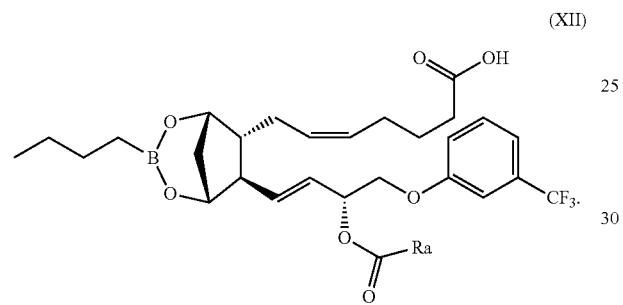

(XII)

Compounds of formula (XII), wherein Ra is as above defined, can be generally prepared by reacting a compound of formula (XIII) with compounds of formula (Va-c):

(Va) =XOC—(CHR¹)—NH—(C=O)—(CH₂)$_m$—[O—(CH₂)$_n$]$_p$—(CH—ONO₂)$_q$—CH₂—ONO₂

(Vb) =XOC—(CH₂)₂—NH—(C=O)—(CH₂)$_m$—[O—(CH₂)$_n$]$_p$—(CH—ONO₂)$_q$—CH₂—ONO₂

(VC) =XOC—(CH₂)$_m$—[O—(CH₂)$_n$]$_p$—(CH—ONO₂)$_q$—CH₂—ONO₂ wherein X is —Cl, p-nitrophenoxy, pentafluorophenoxy or 2,5-pyrrolidinedione, 1-oxy as depicted in the below reported scheme:

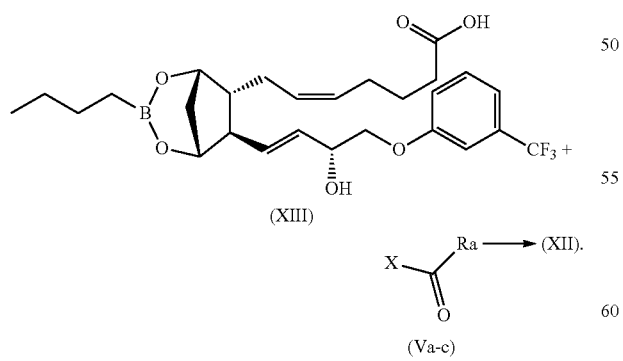

When X=—Cl, the reaction is carried out in presence of a base such as DMAP, pyridine or triethylamine or K₂CO₃, Cs₂CO₃ in an aprotic/non polar solvent such as THF, DMF or CH₂Cl₂, at a temperature ranging from −20° C. to 60° C.

When X is selected from p-nitrophenoxy, pentafluorophenoxy or 2,5-pyrrolidinedione, 1-oxy, the reaction is carried out in a aprotic polar/non polar solvent such as THF, DMF or CH₂Cl₂, in presence of DMAP at temperature ranging from 0° C. to 80° C.

The compound of formula (XIII) can be prepared as already described for analogous compound (III) by reacting a fluprostenol (XIV) with butylboronic acid following a general procedure reported in Organic Syntheses, Coll. Vol. 10, p. 613 (2004).

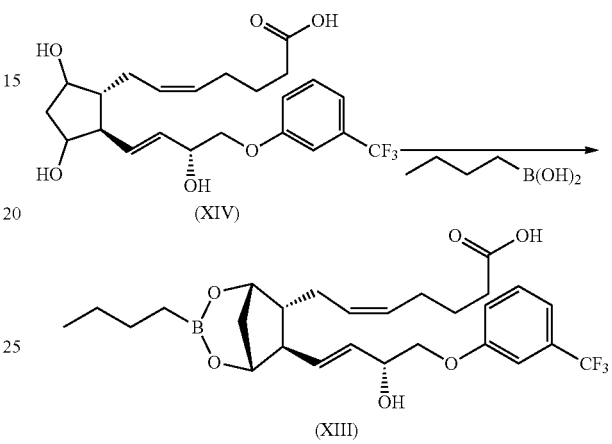

EXAMPLE 1

Synthesis of (Z)-isopropyl 7-((1R,2R,3R,5S)-3,5-dihydroxy-2-((R,E)-3-(6-(nitrooxy) hexanoyloxy)-4-(3-(trifluoromethyl)phenoxy)but-1-enyl)cyclopentyl)hept-5-enoate (Corresponding to Compound (9))

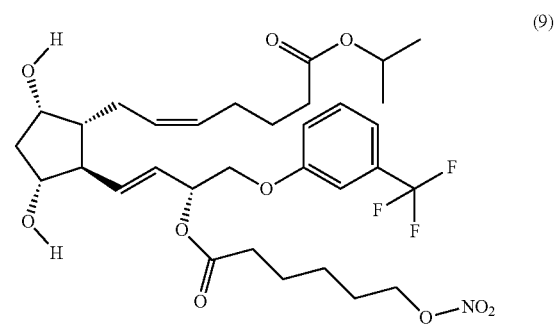 [SMILES: CC(C)OC(=O)CCC/C=C\C[C@@H]1[C@@H](/C=C/[C@H](COc2cccc(C(F)(F)F)c2)OC(=O)CCCCCO[N+](=O)[O-])[C@H](O)C[C@@H]1O]

Step 1: Synthesis of 4-nitrophenyl 6-bromoexanoate

To a solution of 6-bromohexanoic acid (1.0 g, 5.12 mmol) and DCC (1.1 g, 5.33 mmol) in DCM (15 ml), cooled to 0° C., p-nitrophenol (0.713 g, 5.12 mmol) was added portionwise. The mixture was stirred overnight at room temperature. The mixture was then filtered, evaporated and purified by flash chromatography (Gradient: Cy/AcOEt 5% to 50% in 12 CV), yielding 4-nitrophenyl 6-bromoexanoate (1.301 g, 80.3%).

¹H NMR (300 MHz, CDCl₃) δ 8.33-8.21 (m, 2H), 7.33-7.23 (m, 2H), 3.45 (t, J=6.6 Hz, 2H), 2.64 (t, J=7.4 Hz, 2H), 1.93 (dt, J=14.6, 6.8 Hz, 2H), 1.86-1.74 (m, 2H), 1.65-1.54 (m, 2H).

Step 2: Synthesis of 4-nitrophenyl 6-(nitrooxy)hexanoate

To a solution of 4-nitrophenyl 6-bromohexanoate (1.301 g, 4.12 mmol) in CH$_3$CN (30 ml), kept in the dark, AgNO$_3$ (840.85 mg, 4.95 mmol) was added. The mixture was refluxed overnight. Then, the salts were filtered off and the solvent concentrated. EtOAc was added to the residue and the salts filtered off again. The solution was concentrated and the residue purified by flash chromatography (DCM 100%) affording 1.2 g of the 4-nitrophenyl 6-(nitrooxy)hexanoate (Yield: 97.6%).

$^1$H NMR (300 MHz, CDCl$_3$) δ 8.28 (d, J=9.1 Hz, 2H), 7.28 (d, J=9.5 Hz, 2H), 4.49 (t, J=6.4 Hz, 2H), 2.64 (t, J=7.3 Hz, 2H), 1.82 (q, J=7.7 Hz, 4H), 1.56 (td, J=8.7, 4.1 Hz, 2H).

Step 3: Synthesis of (Z)-isopropyl 7-((1R,5S,6R,7R)-3-butyl-7-((R,E)-3-hydroxy-4-(3-(trifluoromethyl)phenoxy)but-1-enyl)-2,4-dioxa-3-borabicyclo[3.2.1]octan-6-yl)hept-5-enoate

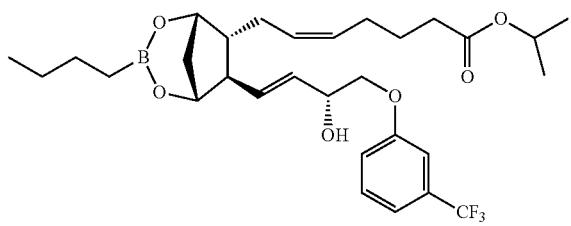 [SMILES: CCCCB1O[C@H]2C[C@@H](O1)[C@H](/C=C/[C@@H](O)COc1cccc(C(F)(F)F)c1)[C@H]2C/C=C\CCCC(=O)OC(C)C]

The compound was prepared following a procedure reported in Organic Syntheses, Coll. Vol. 10, p. 613 (2004).

To a solution of fluprostenol isopropyl ester (0.5 g, 1.0 mmol) in Et$_2$O (3 ml) and DCM (1 ml), butylboronic acid (0.1 g, 1.0 mmol) was added. After stirring for a few minutes, some molecular sieves (4 Å) were added. The mixture was stirred 5 h at room temperature. The reaction was controlled in TLC (Cy/AcOEt 7:3) using alumina. Because the reaction was not finished, a second aliquot of butylboronic acid (0.05 g, 0.5 mmol) was added and the reaction was stirred overnight. Then the mixture was filtered and concentrated affording the title compound (0.55 mg, Yield: 97%).

$^1$H NMR (300 MHz, Chloroform-d) δ 7.49-7.35 (m, 1H), 7.32-7.00 (m, 3H), 5.81-5.53 (m, 2H), 5.53-5.33 (m, 2H), 5.10-4.90 (m, 1H), 4.61-4.46 (m, 1H), 4.34 (s, 1H), 4.16 (s, 1H), 4.08-3.82 (m, 2H), 2.58-2.38 (m, 1H), 2.38-2.19 (m, 3H), 2.18-2.04 (m, 2H), 2.06-1.93 (m, 1H), 1.92-1.56 (m, 4H), 1.50-1.06 (m, 9H), 1.03-0.75 (m, 4H), 0.74-0.65 (m, 2H).

Step 4: Synthesis of (Z)-isopropyl 7-((1R,2R,3R,5S)-3,5-dihydroxy-2-4R,E)-3-(6-(nitrooxy)hexanoyloxy)-4-(3-(trifluoromethyl)phenoxy)but-1-enyl)cyclopentyl)hept-5-enoate (Corresponding to Compound (9))

(Z)-isopropyl 7-((1R,5S,6R,7R)-3-butyl-7-((R,E)-3-hydroxy-4-(3-(trifluoromethyl)phenoxy)but-1-enyl)-2,4-dioxa-3-borabicyclo[3.2.1]octan-6-yl)hept-5-enoate (prepared in Step 3) (0.50 g, 0.88 mmol) and 4-nitrophenyl 6-(nitrooxy)hexanoate (prepared in Step 2) (0.316 g, 1.01 mmol) and DMAP (0.107 g, 0.88 mmol) were dissolved in DCM (15 ml). The mixture was stirred for 6 hrs at room temperature. Then DMAP (0.53 g, 0.44 mmol) was added and the mixture was stirred overnight. The mixture was then evaporated and redissolved in MeOH and stirred for 4 hrs at room temperature. Then the mixture was evaporated and purified by flash chromatography (Cyclohexane:EtOAc from 8:2 to 4:6) yielding the title compound as a clear oil (0.35 g, 71.4% yield).

EXAMPLE 2

Synthesis of (Z)-isopropyl 7-((1R,2R,3R,5S)-2-((R,E)-3-((S)-5,6-bis(nitrooxy) hexanoyloxy)-4-(3-(trifluoromethyl)phenoxy)but-1-enyl)-3,5-dihydroxycyclopentyl)hept-5-enoate (Corresponding to Compound (10), (S)-isomer)

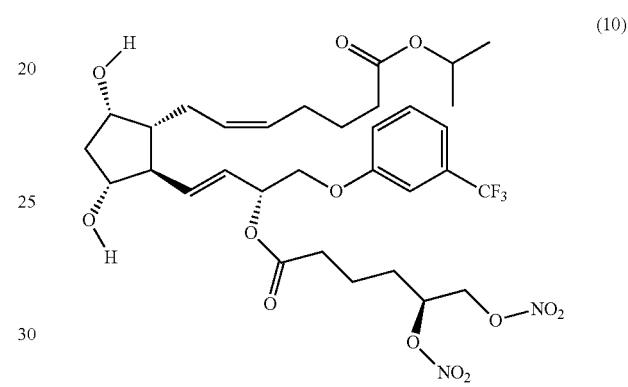

Step 1: Synthesis of Hex-5-enyl-4-nitrobenzoate

To a stirred solution of hex-5-enol (21.25 g, 200 mmol) and 4-nitrobenzoyl chloride (37.11 g, 200 mmol) in DCM (300 mL) at 0° C., triethylamine (28 mL, 200 mmol) was added. The reaction was stirred at room temperature for 4 h and washed with water, HCl 1M, water and brine. The solvent was removed under reduced pressure to give a crude oil which was treated with n-hexane to give a solid that was filtered off. The mother liquor was evaporated to give the title compound as yellow oil (41 g, 82%).

MS: m/z=250 [M+H]$^+$

TLC: DCM 100% R$_f$=0.4

Step 2: Synthesis of (5S)-5,6-dihydroxyhexyl 4-nitrobenzoate

A stirred solution of AD-Mix α (50 g) in a mixture tBuOH/H$_2$O (227 mL each) was stirred for 10 min at room temperature and then cooled to 4° C. After 15 min, hex-5-enyl 4-nitrobenzoate (Step 1) (8.8 g, 35.5 mmol) was added and the reaction stirred overnight at 4° C. Then EtOAc (200 mL) was added and followed by careful addition of sodium metabisulfite (12 g). The reaction was left for 30 min at 4° C. and then treated with water (200 mL). The two layers were separated and the aqueous phase extracted twice with ethyl acetate (2×100 mL). The combined organic phases were washed with water and brine, dried over sodium sulfate, evaporated to give a white solid (9.7 g, 97%).

The residue was dissolved in diethylether (100 mL) and stirred overnight to give the title compound as white solid (8.1 g, 84%).

MS: 284 [M+H]$^+$

TLC: (DCM/MeOH-0.5%) R$_f$=0.36

Step 3: Synthesis of (5S)-5,6-bis(nitrooxy)hexyl 4-nitrobenzoate

To a stirred solution of fuming HNO₃ (3.6 mL, 88 mmol) in DCM (3 mL) at 0° C., was added acetic anhydride (13.7 mL) and after 10 minutes of stirring, a solution of (5S)-5,6-dihydroxyhexyl 4-nitrobenzoate (Step 2) (5 g, 17.6 mmol) in dichloromethane (2 mL) was added and the reaction stirred at this temperature for 60 min. The crude mixture was then poured on ice and the organic layer extracted, washed with water, brine, dried over sodium sulfate, evaporated to give the title compound as pale yellow oil (6.4 g, 99%). The residue obtained was used in the next step without further purification.

MS: 374 [M+H]⁺

TLC: (DCM 100%) $R_f$=0.37

Step 4: Synthesis of (2S)-6-hydroxy-2-(nitrooxy)hexyl nitrate

To a stirred solution of (5S)-5,6-bis(nitrooxy)hexyl 4-nitrobenzoate (Step 3) (7.4 g, 19.82 mmol) in a 1/1 mixture of ethanol/THF (33 mL of each) at 0° C., a 2 M NaOH solution (19.8 mL, 2 eq) was added and the reaction was stirred for 2 h. The reaction was diluted with ethyl acetate and water (100 mL of each) and extracted. The organic layer was successively washed with water and brine, dried over sodium sulfate and evaporated. The oily residue was purified by column chromatography (gradient system from 4/6 ethyl acetate/Cy to 60/40 ethyl acetate/Cy) to give the title compound as colorless oil (4.1 g, 92%).

TLC: (EtOAc/Cy-50%) $R_f$=0.31

Step 5: Synthesis of (5S)-5,6-bis(nitrooxy)hexanoic acid

To a solution of (2S)-6-hydroxy-2-(nitrooxy)hexyl nitrate (Step 4) (3 g, 13.4 mmol) and Sodium periodate (8.4 g, 40.2 mmol) in CHCl₃, Acetonitrile, H₂O (1:1:1), ruthenium (IV) oxide (180 mg, 1.34 mmol) was added. The mixture was stirred overnight at RT, the precipitate was filtered off and the solvent was removed under reduced pressure. The residue was dissolved in DCM, washed with water, dried with MgSO₄, filtered and concentrated under reduced pressure. The crude was purified by flash chromatography (EtOAc in cyclohexane from 5% to 50%) affording 2.4 g of (5S)-5,6-bis(nitrooxy)hexanoic acid (Yield: 75%)

TLC: (DCM/MeOH-0.5%) $R_f$=0.34

Step 6: Synthesis of (S)-4-nitrophenyl 5,6-bis(nitrooxy)hexanoate

To a solution of (5S)-5,6-bis(nitrooxy)hexanoic acid (1.7 g, 6.76 mmol) and DCC (1.4 g, 6.76 mmol) in DCM (65 ml), p-nitrophenol (0.94 g, 6.76 mmol) was added portion wise. The mixture was stirred overnight at RT. Progress was checked by TLC (Cy/AcOEt 4:6). Once the reaction was complete, the mixture was filtered, evaporated and purified by flash chromatography (Gradient: Cy/AcOEt 10% to 60% in 12 CV), yielding 1.51 (S)-4-nitrophenyl 5,6-bis(nitrooxy) hexanoate (84.3%).

TLC: (Cy/EtOAc-4/6) $R_f$=0.36

Step 7: Synthesis of (Z)-isopropyl 7-((1R,2R,3R,5S)-2-((R,E)-3-((S)-5,6-bis(nitrooxy) hexanoyloxy)-4-(3-(trifluoromethyl)phenoxy)but-1-enyl)-3,5-dihydroxycyclopentyl)hept-5-enoate (Corresponding to Compound (10) (S)-isomer)

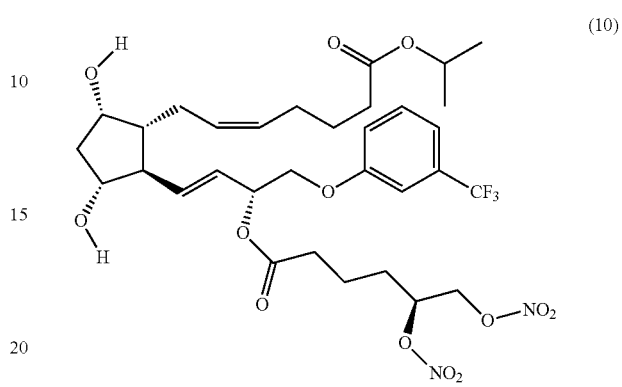

(Z)-isopropyl 7-((1R,5S,6R,7R)-3-butyl-7-4R,E)-3-hydroxy-4-(3-(trifluoromethyl) phenoxy)but-1-enyl)-2,4-dioxa-3-borabicyclo[3.2.1]octan-6-yl)hept-5-enoate (prepared in Example 1, Step 3) (0.50 g, 0.88 mmol) and (S)-4-nitrophenyl 5,6-bis(nitrooxy)hexanoate (prepared in Step 6) (0.37 g, 1.01 mmol) and DMAP (0.110 g, 0.88 mmol) were dissolved in DCM (15 ml). The mixture was stirred for 6 hrs at room temperature. Then DMAP (0.53 g, 0.44 mmol) was added and the mixture was stirred overnight. The mixture was then evaporated and redissolved in MeOH and stirred for 4 hrs at room temperature. Then the mixture was evaporated and purified by flash chromatography (Cyclohexane:EtOAc from 9:1 to 1:1) yielding the title compound as a clear oil (0.310 g, 49.6% yield).

EXAMPLE 3

Synthesis of (Z)-isopropyl 7-((1R,2R,3R,5S)-3,5-dihydroxy-2-((R,E)-3-(2-(2-(nitrooxy)ethoxy)acetoxy)-4-(3-(trifluoromethyl)phenoxy)but-1-enyl) cyclopentyphept-5-enoate (Corresponding to Compound (11))

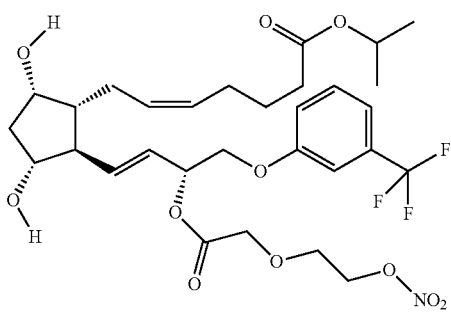 [SMILES: CC(C)OC(=O)CCC/C=C\C[C@@H]1[C@@H](/C=C/[C@H](COc2cccc(C(F)(F)F)c2)OC(=O)COCCO[N+](=O)[O-])[C@H](O)C[C@@H]1O]

Step 1: Synthesis of 2-(2-hydroxyethoxy)ethyl nitrate

A solution of ethylene glycol (4.0 g, 37.7 mmol) in DCM (200 ml) was cooled to −30° C. and a mixture of HNO₃ (1.6 ml, 37.7 mmol) in Ac₂O (10.7 ml, 113 mmol) was added dropwise under vigorous stirring. The mixture was stirred 2 hours at room temperature and then poured into ice. The organic phase was evaporated. The aqueous phase was neutralized to pH 7 with NaHCO₃ and then extracted 3 times with cyclohexane and 3 times with DCM. The DCM layer only was dried over Na$_2$SO$_4$ and evaporated to give the desired product (2.9 g, Yield: 50%) that was used in the next step without further purification.

$^1$H NMR (300 MHz, Chloroform-d) δ 4.70-4.56 (m, 2H), 3.84-3.71 (m, 4H), 3.65-3.55 (m, 2H).

Step 2: Synthesis of 2-(2-(nitrooxy)ethoxy)acetic acid

To a solution of 2-(2-hydroxyethoxy) ethyl nitrate (2.9 g, 18.9 mmol) in acetone (100 ml) cooled at 0° C., NaHCO$_3$ saturated solution (75 ml), NaBr (0.8 g, 7.6 mmol) and TEMPO (0.6 g, 3.8 mmol) were added. Trichloroisocyanuric acid (8.8 g, 37.9 mmol) was then added portionwise. The reaction was allowed to reach room temperature and stirred for 3 hours. The mixture was cooled to 0° C. and 20 ml of isopropanol were added slowly. The mixture was stirred at 0° C. for 30 min. The formation of a white solid was observed. The precipitate was filtered off and the solvent concentrated. The residue was basified with NaOH 2N (pH≈12) and washed twice with EtOAc. To the aqueous phase HCl 1N was added until pH 2-3 and then extracted five times with EtOAc. The organic phase was dried over Na$_2$SO$_4$ and then was evaporated. A white solid was observed. The solid was digested with DCM/MeOH 95:5. The solution was then evaporated affording the title compound as a brown oil. (2.26 g, Yield: 72%)

$^1$H NMR (300 MHz, Chloroform-d) δ 4.70-4.54 (m, 2H), 4.19 (s, 2H), 3.92-3.76 (m, 2H).

Step 3: Synthesis of 4-nitrophenyl 2-(2-(nitrooxy)ethoxy)acetate

To a solution of 2-(2-(nitrooxy)ethoxy)acetic acid (Step 2) (0.9 g, 5.3 mmol) and DCC (1.093 g, 5.3 mmol) in DCM, p-nitrophenol (0.8 g, 5.83 mmol) was added portionwise. The mixture was stirred overnight at room temperature. The mixture was filtered, evaporated and purified by flash chromatography (Biotage SP4 instrumentation EtOAc in cyclohexane from 5% to 50% in 12 CV) yielding the title compound (1.43 g, 94.3%).

Step 4: Synthesis of (Z)-isopropyl 7-((1R,2R,3R,5S)-3,5-dihydroxy-2-((R,E)-3-(2-(2-(nitrooxy)ethoxy)acetoxy)-4-(3-(trifluoromethyl)phenoxy)but-1-enyl)cyclopentyl)hept-5-enoate (Corresponding to Compound (11))

(Z)-isopropyl7-((1R,5S,6R,7R)-3-butyl-7-((R,E)-3-hydroxy-4-(3 (trifluoromethyl) phenoxy)but-1-enyl)-2,4-dioxa-3-borabicyclo[3.2.1]octan-6-yl)hept-5-enoate (Example 1, Step 3) (0.55 g, 1.0 mmol) and 4-nitrophenyl 2-(2-(nitrooxy)ethoxy)acetate (0.81 g, 2.8 mmol) and DMAP (0.72 g, 3.6 mmol) were dissolved in DCM (3 ml). The mixture was stirred for a few minutes and some molecular sieves 4 Å were added. The mixture was stirred 48 h and then filtered. The filtrate was then purified by preparative HPLC. The product was treated with aqueous NaHCO$_3$ in order to remove TFA and the aqueous phase extracted 3 times with ethyl acetate, dried over Na$_2$SO$_4$ and the solvent removed in vacuo affording 0.12 g of a pale yellow oil (Yield: 20%).

$^1$H NMR (300 MHz, DMSO-d6) δ 7.50 (t, 1H), 7.33-7.19 (m, 3H), 5.75-5.49 (m, 3H), 5.47-5.34 (m, 1H), 5.30-5.14 (m, 1H), 4.93-4.72 (m, 1H), 4.71-4.55 (m, 3H), 4.39 (d, 1H), 4.28-4.09 (m, 4H), 3.94-3.60 (m, 4H), 2.31-1.82 (m, 8H), 1.55-1.18 (m, 4H), 1.12 (d, 6H).

EXAMPLE 4

Synthesis of (Z)-isopropyl 7-((1R,2R,3R,5S)-2-((R,E)-3-(3-((S)-2,3-bis (nitrooxy)propoxy)propanoyloxy)-4-(3-(trifluoromethyl)phenoxy)but-1-enyl)-3,5-dihydroxycyclopentyl)hept-5-enoate (Corresponding to Compound (12), (S)-isomer)

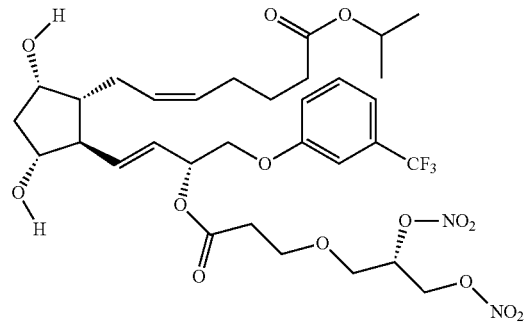 [SMILES: CC(C)OC(=O)CCC/C=C\C[C@@H]1[C@@H](/C=C/[C@H](COc2cccc(C(F)(F)F)c2)OC(=O)CCOC[C@@H](CO[N+](=O)[O-])O[N+](=O)[O-])[C@H](O)C[C@@H]1O]

Step 1: Synthesis of (S)-4-(allyloxymethyl)-2,2-dimethyl-1,3-dioxolane

NaH (60%) (3.4 g; 85.54 mmol) was suspended in dry THF (140 ml) together with S(+) 1,2-Isopropylidenglycerol (5.65 g; 42.75 mmol) and 15-Crown-5 (0.9 g; 4.28 mmol). The mixture was cooled to 0° C. and allyl bromide (7.2 ml; 85.54 mmol) was added dropwise. The suspension was stirred for 6 h at R.T, than NH$_4$Cl saturated solution (100 ml) was added dropwise at 0° C. and then the mixture extracted with Et$_2$O (3×100 ml). The combined organic layers were washed once with brine and concentrated under reduced pressure carefully. The residue was purified by flash chromatography (Biotage SP4 instrument, SNAP 100 column, isocratic elution Et$_2$O/Cyclohexane 1:9), affording 5.8 g, (yield 78.5%) of the title compound.

$^1$H NMR (300 MHz, Chloroform-d) δ 6.00-5.78 (m, 1H), 5.35-5.13 (m, 2H), 4.35-4.21 (m, 1H), 4.11-3.98 (m, 3H), 3.73 (m, 1H), 3.57-3.40 (m, 2H), 1.51-1.32 (m, 6H).

Step 2: Synthesis of (S)-3-((2,2-dimethyl-1,3-dioxolan-4-yl)methoxy)propan-1-ol

To a stirred solution of (S)-4-(allyloxymethyl)-2,2-dimethyl-1,3-dioxolane (2.0 g, 10.64 mmol) in dry THF (180 ml) cooled at 0° C., 9BBN 0.5M (241.8 ml, 121 mmol) was added dropwise. The reaction was stirred 30 minutes at 0° C. and overnight at room temperature. The reaction mixture was cooled at 0° C. and NaOH 2N (84 ml) was added together with H$_2$O$_2$ 30% (58 ml). The mixture was diluted with Et$_2$O (100 ml) and NaOH 1N (100 ml). The 2 phases were separated and aqueous layer was extracted with Et$_2$O (3×120 ml). The combined organic layers were washed once with brine, dried over Na$_2$SO$_4$ and concentrated under reduced pressure. The residue was purified by flash chromatography (Biotage SP4 instrument, SNAP 100 column, EtOAC in cyclohexane, from 30% to 80% in 10 c.v. affording 6.4 g (yield: 100%) of the title compound.

$^1$H NMR (300 MHz, Chloroform-d) δ 4.35-4.20 (m, 1H), 4.11-4.01 (m, 1H), 3.85-3.63 (m, 5H), 3.58-3.46 (m, 2H), 1.97-1.80 (m, 2H), 1.45 (s, 3H), 1.38 (s, 3H).

Step 3: Synthesis of (S)-3-((2,2-dimethyl-1,3-dioxolan-4-yl)methoxy)propanoic acid To a solution of (S)-3-((2,2-dimethyl-1,3-dioxolan-4-yl)methoxy)propan-1-ol (2.03 g; 10.51 mmol) in acetone (50 ml) cooled at 0° C., NaHCO₃ sat solution (56 ml), NaBr (0.45 g, 4.20 mmol) and TEMPO (0.34 g, 2.10 mmol) were added. Trichloroisocyanuric acid (4.91 g, 21.02 mmol) was then added portionwise. The mixture was allowed to reach room temperature and stirred for 3 h. The mixture was then cooled at 0° C. and isopropanol (20 ml) was added slowly. The mixture was stirred at 0° C. 30 minutes. The formation of a white solid was observed. The precipitate was filtered off and the solvent concentrated. NaOH 2N was added to the residue (pH≈12) and the aqueous solution was washed twice with EtOAc. To the aqueous phase HCl 1N was added until pH 2-3 and it was extracted with EtOAc (5×50 ml). The combined organic phases was dried over Na₂SO₄ and then evaporated affording 0.82 g (Yield: 38%) of the title compound.

$^1$H NMR (300 MHz, Chloroform-d) δ 4.34-4.16 (m, 1H), 4.11-3.97 (m, 1H), 3.85-3.68 (m, 3H), 3.63-3.42 (m, 2H), 2.74-2.55 (m, 2H), 1.41 (s, 3H), 1.35 (s, 3H).

Step 4: Synthesis of (S)-4-nitrophenyl 3-((2,2-dimethyl-1,3-dioxolan-4-yl) methoxy) propanoate To a solution of (S)-3-((2,2-dimethyl-1,3-dioxolan-4-yl) methoxy) propanoic acid (0.82 g, 4.02 mmol), DCC (0.83 mg, 4.02 mmol) and DMAP (0.1 g, 0.80 mmol) in DCM (15 ml), 4-nitrophenol (0.56 g; 4.02 mmol) was added portionwise. The mixture was stirred overnight at room temperature, then the precipitate was filtered off and the solvent evaporated. The residue was purified by flash chromatography (Biotage SP4 instrument, EtOAc in cyclohexane from 5% to 50% in 12 CV) affording 0.97 g of the title compound (Yield: 74%). $^1$H NMR (300 MHz, Chloroform-d) δ 8.33-8.21 (m, 2H), 7.37-7.20 (m, 2H), 4.37-4.20 (m, 1H), 4.09-4.00 (m, 1H), 3.96-3.84 (m, 2H), 3.80-3.66 (m, 1H), 3.63-3.47 (m, 2H), 2.96-2.78 (m, 2H), 1.42 (s, 3H), 1.36 (s, 3H).

Step 5: Synthesis of (R)-4-nitrophenyl 3-(2,3-dihydroxypropoxy) propanoate

To a stirred solution of (S)-4-nitrophenyl 3-((2,2-dimethyl-1,3-dioxolan-4-yl) methoxy) propanoate (0.97 g, 2.97 mmol) in THF (10 ml), HCl 3N (2 ml) was added and the solution stirred for 4 h at room temperature. Then EtOAc (5 ml) and H₂O (5 ml) were added and the two phases were separated. The aqueous phase was extracted with EtOAc (2×5 ml). The combined organic layers were washed with brine, dried over Na₂SO₄ and concentrated under reduced pressure affording 0.89 g of the title compound, which was used in the next step without further purification.

Step 6: Synthesis of (S)-4-nitrophenyl 3-(2,3-bis(nitrooxy)propoxy) propanoate To a solution of Ac₂O (0.76 ml, 8.07 mmol) in DCM (5 ml) at −40° C., fuming HNO₃ (0.38 ml, 9.32 mmol) was added dropwise. A solution of (R)-4-nitrophenyl 3-(2,3-dihydroxypropoxy) propanoate (0.89 g, 3.11 mmol) in DCM (7 ml) was then added dropwise. The mixture was allowed to reach 0° C. and stirred for 4 hours. The mixture was then poured into ice and NaHCO₃ was added portionwise. The two phases were separated and the aqueous phase washed twice with DCM. The combined organic phases were dried over Na₂SO₄ and concentrated affording 0.56 g of the title compound (yield of two steps: 38%).

$^1$H NMR (300 MHz, Chloroform-d) δ 8.35-8.22 (m, 2H), 7.35-7.22 (m, 2H), 5.48-5.34 (m, 1H), 4.88-4.73 (m, 1H), 4.73-4.56 (m, 1H), 3.94-3.85 (m, 2H), 3.85-3.77 (m, 2H), 2.88 (t, 2H).

Step 7: Synthesis of (Z)-isopropyl 7-((1R,2R,3R, 5S)-2-4R,E)-3-(3-((S)-2,3-bis(nitrooxy)propoxy) propanoyloxy)-4-(3-(trifluoromethyl)phenoxy)but-1-enyl)-3,5-dihydroxycyclopentyl)hept-5-enoate (Corresponding to Compound (12), (S)-isomer)

To a solution of (Z)-isopropyl 7-((1R,5S,6R,7R)-3-butyl-7-((R,E)-3-hydroxy-4-(3-(trifluoromethyl)phenoxy)but-1-enyl)-2,4-dioxa-3-borabicyclo[3.2.1]octan-6-yl)hept-5-enoate (step 3, example 1) (0.25 g, 0.44 mmol) and (S)-4-nitrophenyl 3-(2,3-bis(nitrooxy)propoxy) propanoate (0.24 g, 0.66 mmol) in DCM (1 ml), DMAP (0.34 g, 1.67 mmol) and molecular sieves 4 Å were added. The mixture was stirred 48 h at room temperature and then the molecular sieves filtered off. The solvent was removed under reduced pressure and the residue was purified by HPLC preparative. NaHCO₃ saturated solution was added to the product and the aqueous phase was extracted twice with DCM. The product was treated with aqueous NaHCO₃ in order to remove TFA and the aqueous phase extracted 3 times with ethyl acetate, dried over Na₂SO₄ and the solvent removed in vacuo affording the title compound as a pale yellow oil (0.17 g, Yield: 52%).

$^1$H NMR (300 MHz, DMSO-d₆) δ 7.59-7.41 (m, 1H), 7.37-7.13 (m, 3H), 5.73-5.45 (m, 3H), 5.47-5.32 (m, 1H), 5.28-5.11 (m, 1H), 4.95-4.75 (m, 2H), 4.75-4.62 (m, 1H), 4.62-4.50 (d, 1H), 4.44-4.33 (d, 1H), 4.24-4.07 (m, 2H), 4.94-3.82 (m, 1H), 3.77-3.54 (m, 4H), 2.56 (t, 2H), 2.29-2.09 (m, 3H), 2.09-1.98 (m, 1H), 1.98-1.82 (m, 3H), 1.57-1.36 (m, 3H), 1.36-1.19 (m, 1H), 1.12 (d, 6H).

EXAMPLE 5

Synthesis of (Z)-isopropyl 7-((1R,2R,3R,5S)-3,5-dihydroxy-2-((R,E)-3-(3-(6-(nitrooxy) hexanamido) prop anoyl oxy)-4-(3-(trifluoromethyl)phenoxy)but-1-enyl)cyclopentyl)hept-5-enoate (Corresponding to Compound (1))

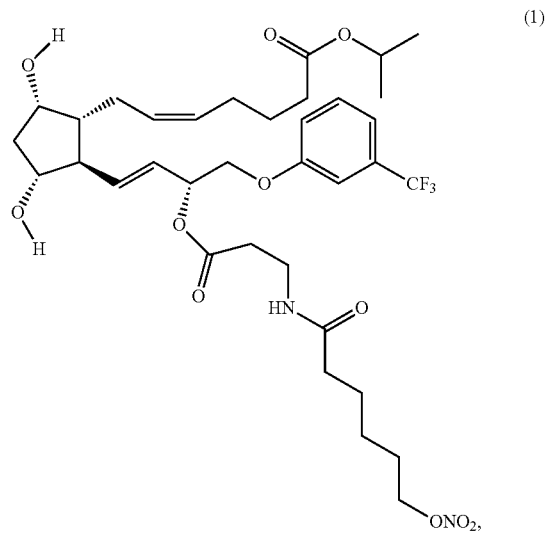

(1)

Step 1: Synthesis of t-butyl-3-(6-(nitrooxy)hexanamido)propanoate

To a solution of 4-nitrophenyl 6-(nitrooxy)hexanoate (prepared as described in Example 1, Step 2), (1.4 g, 4.68 mmol) and ß-ala-OtBu hydrochloride (0.85 g, 4.68 mmol) in DMF (10 ml) cooled at 0° C., TEA (1.3 ml, 9.36 mmol) was added dropwise. The solution was stirred for 15 minutes and DMAP (61 mg, 0.47 mmol) was added. The solution was stirred at rt overnight and the solvent removed under reduce pressure. The crude was dissolved in diethyleter and washed with HCl 1M to remove DMAP and TEA. The organic layer was washed with NaOH 1M to remove p-nitrophenol, washed with water, brine, dried over sodium sulfate an then evaporated to give 1.2 g, of the title compound as a pale yellow oil (Yield: 90%). The obtained residue was used in the next step without any further purification.

MS: 305 [M+H]$^+$

TLC: (Cy:EtOAc 7:3) R$_f$=0.36

Step 2: Synthesis of 3-(6-(nitrooxy)hexanamido)propanoic acid

To a stirred solution of t-butyl-3-(6-(nitrooxy)hexanamido)propanoate (1 g, 3.3 mmol) in DCM (5 mL) at 0° C., was added BF3.Et2O (0.5 mL, 4 mmol) in 10 min, and the solution was stirred at rt for 3 h. The crude mixture was then poured on brine and the organic layer separated, dried over sodium sulfate and evaporated to give 0.820 g of the title compound as a pale yellow oil (100%). The obtained residue was used in the next step without any further purification.

MS: 249 [M+H]$^+$

Step 3: Synthesis of 4-nitrophenyl 3-(6-(nitrooxy)hexanamido)propanoate

To a solution of 3-(6-(nitrooxy)hexanamido)propanoic acid (0.820 g, 3.3 mmol) and DCC (0.681 g, 3.3 mmol) in DCM (30 ml), p-nitrophenol (0.505 g, 3.63 mmol) was added portion wise. The mixture was stirred overnight at rt. Then the mixture was filtered, evaporated and purified by flash chromatography (Gradient: Cy/AcOEt 5% to 70% in 12 CV), giving 1.1 g of the title compound (Yield: 91%).

MS: 370 [M+H]$^+$

TLC: (Cy:EtOAc 4:6) R$_f$=0.35

Step 4: Synthesis of (Z)-isopropyl 7-((1R,2R,3R, 5S)-3,5-dihydroxy-2-((R,E)-3-(3-(6-(nitrooxy) hexanamido) propanoyloxy)-4-(trifluoromethyl) phenoxy)but-1-enyl)cyclopentyl)hept-5-enoate (Corresponding to Compound (1))

To a solution of (Z)-isopropyl 7-((1R,5S,6R,7R)-3-butyl-7-((R,E)-3-hydroxy-4-(3-(trifluoromethyl)phenoxy)but-1-enyl)-2,4-dioxa-3-borabicyclo[3.2.1]octan-6-yl)hept-5-enoate (Example 1, Step 3) (220 mg, 0.39 mmol) and 4-nitrophenyl 3-(6-(nitrooxy)hexanamido)propanoate (158 mg, 0.43 mmol) in dry DCM (10 ml), DMAP (41 mg, 0.39 mmol) was added dropwise and the mixture was stirred for 72 hrs. The solvent was removed under reduced pressure and the product was dissolved in MeOH and stirred for 4 hrs at rt. The mixture was then evaporated and purified by reverse phase chromatography (H2O:CH3CN 8:2 to 1:1) affording 0.151 g of the title compound as a clear oil (Yield: 53%).

$^1$H NMR: (600 MHz, DMSO-d6) δ 7.87 (t, 1H), 7.52 (t, 1H), 7.30 (d, 1H), 7.25 (d, 2H), 5.67 (dd, 1H), 7.59-7.53 (m, 2H), 5.43 (m, 1H), 5.23 (m, 1H), 4.84 (m, 1H), 4.62 (d, 1H), 4.47 (t, 2H), 4.40 (d, 1H), 4.18 (m, 2H), 4.90 (m, 1H), 3.69 (m, 1H), 3.27 (m, 2H), 2.47 (t, 2H), 2.24-1.91 (m, 10H), 1.61 (m, 2H), 1.53-1.41 (m, 5H), 1.36-1.22 (m, 4H), 1.14 (dd, 6H).

MS: m/z=731 [M+H]$^+$

EXAMPLE 6

Synthesis of (Z)-isopropyl 7-((1R,2R,3R,5S)-2-((3R,E)-3-(3-(5,6-bis(nitrooxy)hexanamido) propanoyloxy)-4-(3-(trifluoromethyl)phenoxy)but-1-enyl)-3,5-dihydroxycyclopentyl) hept-5-enoate (Corresponding to Compound (2), (S)-isomer)

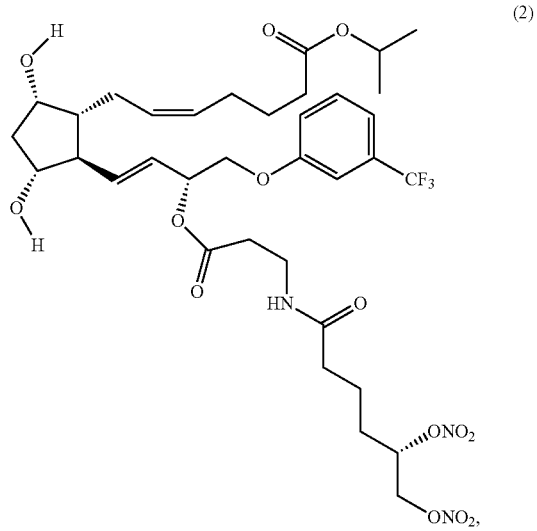

(2)

Step 1: Synthesis of tert-butyl 3-{[5,6-bis(nitrooxy) hexanoyl]amino}propanoate

To a solution of (5S)-5,6-bis(nitrooxy)hexanoic acid (Example 2, Step 5) (1.4 g, 4.68 mmol) and ß-ala-OtBu hydrochloride (0.85 g, 4.68 mmol) in DMF (10 ml) cooled at 0° C., TEA (1.3 ml, 9.36 mmol) was added dropwise. The solution was stirred for 15 minutes, then DCC (0.96 g, 4.68 mmol) and DMAP (61 mg, 0.47 mmol) were added. The solution was stirred at rt overnight. Then the solvent was removed under reduce pressure and the crude was dissolved in diethyleter and washed with HCl 1M to remove DMAP and TEA. The organic layer was washed with water, brine, dried over sodium sulfate, then evaporated affording 1.2 g of the title compound as a pale yellow oil (Yield: 90%). It was used in the next step without further purification.

MS: 366 [M+H]$^+$

TLC: (Cy:EtOAc 7:3) Rf=0.37

Step 2: Synthesis of 3-{[(5S)-5,6-bis(nitrooxy) hexanoyl]amino}propanoic acid

To a stirred solution of t-butyl-3-(6-(nitrooxy)hexanamido)propanoate (0.5 g, 1.4 mmol) in DCM (2.5 mL) at 0° C., BF$_3$.Et$_2$O (0.3 mL, 1.7 mmol) was added. After 10 min the solution was stirred at rt for 3 hr. The crude mixture was then poured on brine and the organic layer extracted, dried over sodium sulfate, evaporated to give 0.25 g of the desired product as a pale yellow oil (Yield: 58%). The residue obtained was used in the next step without further purification.

MS: 310 [M+H]$^+$

Step 3: Synthesis of 4-nitrophenyl 3-{[(5S)-5,6-bis(nitrooxy)hexanoyl]amino}propanoate To a solution of 3-{[(5S)-5,6-bis(nitrooxy)hexanoyl]amino}propanoic acid (250 mg, 0.81 mmol) and DCC (167 mg, 0.81 mmol) in DCM (8 ml), p-nitrophenol (124 mg, 0.89) was added portion wise and the mixture was stirred overnight at rt. Then the mixture was filtered, evaporated and purified by flash chromatography (Gradient: Cy/AcOEt 5% to 70% in 12 CV), yielding 0.324 g of the desired product. (Yield: 93%).

MS: 431 [M+H]$^+$
TLC: (Cy:EtOAc 1:1) R$_f$=0.35

Step 4: Synthesis of (Z)-isopropyl 7-((1R,2R,3R,5S)-2-((3R,E)-3-(3-(5,6-bis(nitrooxy)hexanamido)propanoyloxy)-4-(3-(trifluoromethyl)phenoxy)but-1-enyl)-3,5-dihydroxycyclopentyl) hept-5-enoate (Corresponding to Compound (2), (S)-isomer)

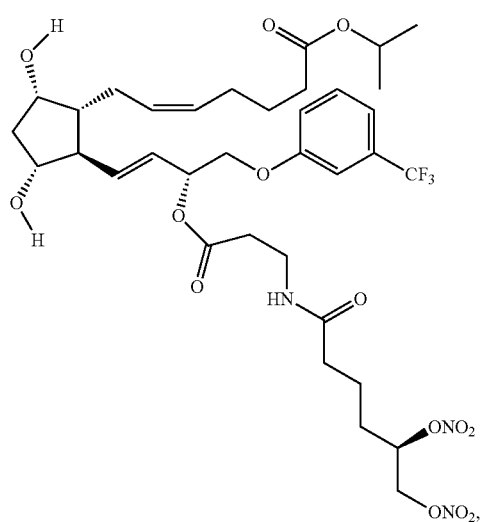
(2)

To a solution of isopropyl (Z)-7-((1R,5S,6R,7R)-3-butyl-7-((R,E)-3-hydroxy-4-(3-(trifluoromethyl)phenoxy)but-1-en-1-yl)-2,4-di oxa-3-borabicyclo[3.2.1]octan-6-yl)hept-5-enoateacid (Example 1, Step 3) (300 mg, 0.53 mmol) and 4-nitrophenyl 3-{[(5S)-5,6-bis(nitrooxy)hexanoyl]amino}propanoate (250 mg, 0.58 mmol) in dry DCM (15 ml), DMAP (65 mg, 0.53 mmol) was added dropwise and the mixture was stirred for 72 hrs. The solvent was removed under reduce pressure and the product was dissolved in MeOH (15 ml) and stirred for 4 hrs at room temperature. Then the mixture was evaporated and purified by C18 chromatography (H$_2$O:CH$_3$CN 8:2 to 1:1) yielding 0.101 g of the title compound as a clear oil (Yield: 24%).

$^1$H NMR: (600 MHz, DMSO-d$_6$) δ 7.92 (t, 1H), 7.51 (t, 1H), 7.29 (d, 1H), 7.25 (d, 2H), 5.67 (dd, 1H), 5.59-5.52 (m, 2H), 5.45-5.35 (m, 2H), 5.22 (m, 1H), 4.90 (dd, 1H), 4.84 (m, 1H), 4.67 (dd, 1H), 4.60 (d, 1H), 4.39 (d, 1H), 4.18 (m, 2H), 3.90 (m, 1H), 3.68 (m, 1H), 3.26 (m, 2H), 2.47 (t, 2H), 2.24-2.13 (m, 4H), 2.06 (m, 3H), 1.94 (m, 3H), 1.70-1.28 (m, 8H), 1.13 (dd, 6H).

MS: m/z=792 [M+H]$^+$
TLC: (H$_2$O:CH$_3$CN 7:3) Rf: 0.28

EXAMPLE 7

Synthesis of (Z)-7-((1R,2R,3R,5S)-2-((R,E)-3-((S)-5,6-bis(nitrooxy)hexanoyloxy)-4-(3-(trifluoromethyl)phenoxy)but-1-enyl)-3,5-dihydroxycyclopentyl)hept-5-enoic acid (Corresponding to Compound (13), (S)-isomer)

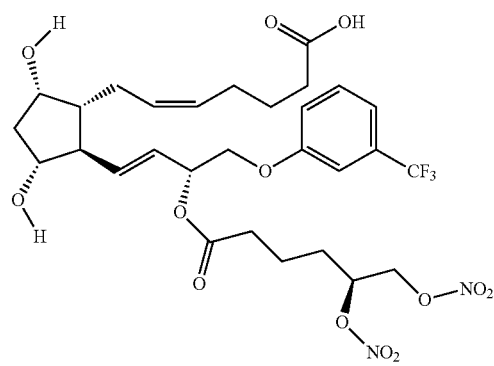 [SMILES: O=C(O)CCC/C=C\C[C@@H]1[C@@H](/C=C/[C@H](COc2cccc(C(F)(F)F)c2)OC(=O)CCC[C@@H](CO[N+](=O)[O-])O[N+](=O)[O-])[C@H](O)C[C@@H]1O]

Step 1: Synthesis of (Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoic acid

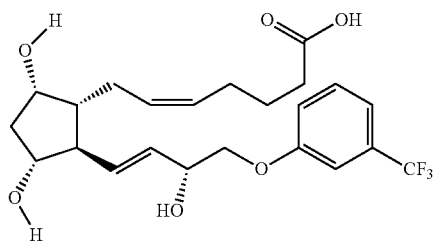 [SMILES: O=C(O)CCC/C=C\C[C@@H]1[C@@H](/C=C/[C@@H](O)COc2cccc(C(F)(F)F)c2)[C@H](O)C[C@@H]1O]

To a solution of fluprostenol isopropyl ester (0.5 g, 1.0 mmol) in a mixture of CH$_2$Cl$_2$/CH$_3$OH (25.5 ml, 9:1 v/v), a methanolic solution of NaOH 2M (2 ml, 4 eq.) was added and the mixture was stirred overnight at RT.

Then water and CH$_2$Cl$_2$ were added to the mixture, and the organic phase was separated to eliminate the unreacted ester. The aqueous layer was acidified to pH 2-3 with HCL 2 N and extracted twice with CH$_2$Cl$_2$. The combined organic layers were dried over Mg$_2$SO$_4$ and the solvent was removed to afford 0.44 g of the title compound (Yield: 97%).

MS: m/z=457 [M−H]$^−$

Step 2: Synthesis of (Z)-7-((1R,5S,6R,7R)-3-butyl-7-((R,E)-3-hydroxy-4-(3-(trifluoromethyl)phenoxy)but-1-en-1-yl)-2,4-dioxa-3-borabicyclo[3.2.1]octan-6-yl)hept-5-enoic acid

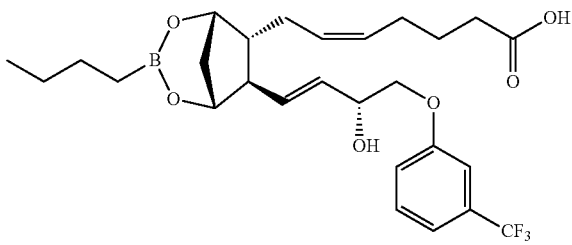 [SMILES: CCCCB1O[C@H]2C[C@@H](O1)[C@H](/C=C/[C@@H](O)COc1cccc(C(F)(F)F)c1)[C@H]2C/C=C\CCCC(=O)O]

To a solution of (Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoic acid (0.44 g, 0.968 mmol) in a mixture of $Et_2O/CH_2Cl_2$ (6.9 ml, 2:1 v/v), butylboronic acid (99 mg, 0.968 mmol) was added. The solution was stirred for 2 minutes, then some molecular sieves (3 Å diameter) were added and the reaction mixture allowed to stir at room temperature for 48 hours. Then the solvent was removed under reduced pressure affording 0.365 g of the title compound (Yield: 72%) that was used in the next step without any further purification.

Step 3: Synthesis of (Z)-7-((1R,2R,3R,5S)-2-((R,E)-3-((S)-5,6-bis(nitrooxy)hexanoyloxy)-4-(3-(trifluoromethyl)phenoxy)but-1-enyl)-3,5-dihydroxycyclopentyl)hept-5-enoic acid (Corresponding to Compound (13), (S)-isomer)

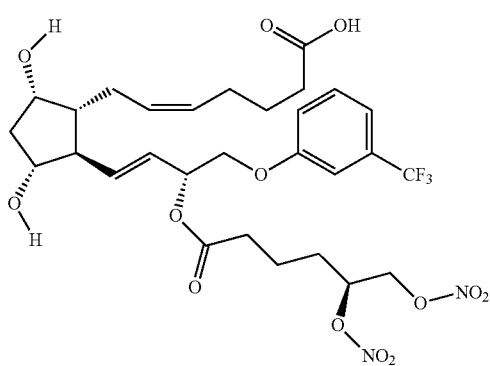 [SMILES: O=C(O)CCC/C=C\C[C@@H]1[C@@H](/C=C/[C@H](COc2cccc(C(F)(F)F)c2)OC(=O)CCC[C@@H](CO[N+](=O)[O-])O[N+](=O)[O-])[C@H](O)C[C@@H]1O]

A mixture of (Z)-7-((1R,5S,6R,7R)-3-butyl-7-((R,E)-3-hydroxy-4-(3-(trifluoromethyl)phenoxy)but-1-en-1-yl)-2,4-dioxa-3-borabicyclo[3.2.1]octan-6-yl)hept-5-enoic acid (0.365 g, 0.696 mmol), 4-nitrophenyl (S)-5,6-bis(nitrooxy) hexanoate (Example 2, Step 6) (0.30 mg, 0.835 mmol) and 4-dimethylaminopyridine (85 mg, 0.696 mmol) in $CH_2Cl_2$ (5 ml) was allowed to stir overnight at room temperature. Then other 85 mg (0.696 mmol) of DMAP were added, and the mixture was stirred for further 24 hours. The solvent was then removed under reduced pressure and the residue was dissolved in $CH_3CN/H_2O$ (8:2 v/v) with 0.01% formic acid mixture and stirred at rt for 4 hours.

The solution was then concentrated and the mixture purified by reversed-phase chromatography ($CH_3CN/H_2O$ from 5:95 to 50:50). The collected product was further purified by flash chromatography (ethyl acetate/cyclohexane 8:2 with 1% acetic acid), affording 71 mg of the target compound (Yield: 15%).

$^1$H NMR (600 MHz, d6-DMSO) δ 7.51 (t, 1H), 7.30 (d, 1H), 7.27-7.23 (m, 2H), 5.67 (dd, 1H), 5.60-5.53 (m, 2H), 5.45-5.38 (m, 2H), 5.26-5.20 (m, 1H), 4.90 (dd, 1H), 4.66 (dd, 1H), 4.58 (br s, 1H), 4.21 (dd, 1H), 4.17 (dd, 1H), 3.92-3.88 (m, 1H), 3.72-3.67 (m, 1H), 2.44-2.34 (m, 2H), 2.24-2.16 (m, 2H), 2.14 (t, 2H), 2.11-2.04 (m, 1H), 1.98-1.89 (m, 5H), 1.77-1.69 (m, 2H), 1.68-1.60 (m, 2H), 1.53-1.41 (m, 3H), 1.35-1.28 (m, 1H).

MS: m/z=677 [M–H]$^-$

EXAMPLE F1

Intraocular Pressure (IOP) Lowering Activity in Hypertonic Saline-Induced IOP Increase in Rabbits Compounds (9), (10), (11), (12) and (13) of the invention and compounds (A-1) and (B-1) disclosed in WO 2009/136281 were directly compared with fluprostenol isopropyl ester and bimatoprost, in the same model of ocular hypertensive rabbit. The hypotensive effects of the two groups of compounds were independently evaluated at different time points and in different sets of hypertensive rabbits.

Treatment Group A

Test compounds and dose (equimolar to the correspondent parent drug)

Compound (9); 0.04%
Compound (10); 0.043%
Compound (11); 0.039%
Compound (12); 0.044%
Compound (13); 0.041%
Fluprostenol isopropyl ester (parent drug); 0.03%

Vehicle: buffered aqueous solution pH 6, polyoxyl 40 hydrogenated castor oil 5 mg/ml, trometamine 10 mg/ml, boric acid 6 mg/ml, mannitol 40 mg/ml, edetate disodium 0.5 mg/ml and benzalkonium chloride 0.15 mg/mL Method Male New Zealand white rabbits weighing 2.0-2.5 kg were used in the experiments. The transient increase in IOP was induced by the injection of 0.1 ml of hypertonic saline solution (5%) into the vitreous of both eyes.

Intraocular pressure (IOP) was determined using a Tono-Pen VET prior to hypertonic saline injection (basal) and at 30, 60, 120 and 240 min thereafter. Vehicle or tested compound dissolved in the vehicle was instilled immediately after the injection of hypertonic saline into the conjunctival pocket. Eyes were randomly assigned to different treatment groups.

One drop of 0.4% oxybuprocaine hydrochloride (Novesine, Sandoz) was instilled in each eye immediately before each set of pressure measurements.

Treatment Groups B (Prior Art Compounds)

Test Compounds and Dose

Compound (A-1): (1S,2E)-3-{(1R,2R,3 S,5R)-2-[(2Z)-7-(Ethyl amino)-7-oxohept-2-en-1-yl]-3,5-dihydroxycyclopentyl}-1-(2-phenylethyl)prop-2-en-1-yl 4-(nitrooxy) butanoate/0.13%

Compound (B-1): (1S,2E)-3-{(1R,2R,3S,5R)-2-[(2Z)-7-(Ethyl amino)-7-oxohept-2-en-1-yl]-3,5-dihydroxycyclopentyl}-1-(2-phenylethyl)prop-2-en-1-yl 6-(nitrooxy) hexanoate/0.14%

Bimatoprost (parent drug)/0.1%.

Vehicle: tween 80 0.5%, 0.2 mg/ml benzalkonium chloride, 0.3% DMSO in PBS pH 6.7 vehicle-treated eyes at same time point and baseline; Table 1 also reports the maximal IOP reduction of the tested compounds expressed in percentage.

Table 2 shows the IOP lowering activity of each tested compound compared to their parent drug at 60 minutes after topical administration.

As shown in Table 1 the maximal IOP reduction of each compound of the invention is greater than the maximal IOP reduction of the prior art compounds.

As shown in Table 2 the IOP reduction elicited by the compounds of the invention with respect to their parent drug (fluprostenol isopropyl ester) is greater than the IOP reduction elicited by the compounds of the prior art with respect to their parent drug (bimatoprost).

TABLE 1

IOP-lowering activity of the compounds at different time points after topical application in transiently ocular hypertensive New Zealand white rabbits

| | Mean IOP changes vs vehicle and baseline (mmHg) | | | | | | Maximal IOP reduc. |
|---|---|---|---|---|---|---|---|
| Compound | 60 min | 90 min | 120 min | 180 min | 240 min | 300 min | (%) |
| A-1 0.13% | $-0.06 \pm 5.2$ | $0.03 \pm 5.0$ | — | $1.1 \pm 2.8$ | — | $-1.9 \pm 3.2$ | $3 \pm 9$ |
| B-1 0.14% | $-3.9 \pm 2.5$ | $-5.6 \pm 2.8$ | — | $5.3 \pm 1.5$ | — | $-3.9 \pm 1.9$ | $10 \pm 3$ |
| Bimatoprost 0.1% | $-1.8 \pm 2.4$ | $-2.7 \pm 2.0$ | — | $0.8 \pm 1.5$ | — | $0.3 \pm 2.6$ | — |
| Comp. (9) 0.04% | $-6.6 \pm 0.9$ | — | $-8.2 \pm 1.2$ | — | $-2.0 \pm 0.7$ | — | $23 \pm 3$ |
| Comp. (10) 0.043% | $-9.2 \pm 1.0$ | — | $-8.8 \pm 1.2$ | — | $-1.2 \pm 0.8$ | — | $26 \pm 3$ |
| Comp. (11) 0.039% | $-9.7 \pm 0.8$ | — | $-7.4 \pm 0.9$ | — | $-3.2 \pm 0.6$ | — | $37 \pm 4$ |
| Comp. (12) 0.044% | $-7.1 \pm 0.8$ | — | $-9.6 \pm 1.0$ | — | $-2.9 \pm 0.5$ | — | $38 \pm 3$ |
| Comp. (13) 0.41% | $-8.6 \pm 1.2$ | — | $-6.9 \pm 0.9$ | — | $-0.3 \pm 1.0$ | — | $39 \pm 3$ |
| Fluprostenol isopropyl ester 0.03% | $-0.08 \pm 1.2$ | — | $-2.0 \pm 1.3$ | — | $-0.4 \pm 0.9$ | — | — |

Method

Male New Zealand white rabbits weighing 2.0-2.5 kg were used in the experiments. The transient increase in IOP was induced by the injection of 0.1 ml of hypertonic saline solution (5%) into the vitreous of both eyes.

Intraocular pressure (IOP) was determined using a pneumatonometer prior to hypertonic saline injection (basal) and at 30, 60, 90, 180 and 300 min thereafter. Vehicle or tested compound dissolved in the vehicle was instilled immediately after the injection of hypertonic saline into the conjunctival pocket. Eyes were randomly assigned to different treatment groups.

One drop of 0.4% oxybuprocaine hydrochloride (Novesine, Sandoz) was instilled in each eye immediately before each set of pressure measurements.

The intraocular pressure values measured following topical application of the tested compounds are reported in Table 1 expressed as mean IOP change in treated eyes versus

TABLE 2

IOP lowering activity of the compounds compared to parent drug

| Compound | Delta$_{60\ min}$ vs parent drug (mmHg) | IOP$_{60\ min}$ reduction vs vehicle (%) |
|---|---|---|
| (A-1) 0.13% | Not effective | 4 |
| (B-1) 0.14% | $-2.1$ | 7 |
| Bimatoprost 0.1% | 0 | 1 |
| Comp. (9) 0.04% | $-6.5$ | 20 |
| Comp. (10) 0.043% | $-9.1$ | 28 |
| Comp. (11) 0.039% | $-9.6$ | 32 |
| Comp. (12) 0.044% | $-7.0$ | 22 |
| Comp. (13) 0.041% | $-8.5$ | 31 |
| Fluprostenol isopropyl ester 0.03% | 0 | 3 |

The invention claimed is:

1. A compound of formula (I) or a salt thereof

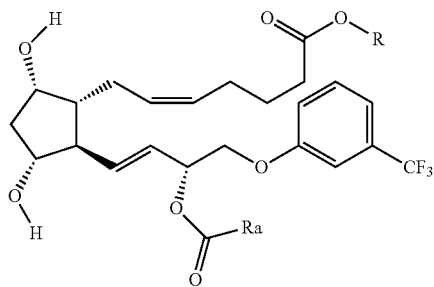
(I)

wherein
R is —CH(CH$_3$)$_2$ or H;
Ra is selected from
A1): —(CHR$^1$)—NH—(C=O)—(CH$_2$)$_m$—[O—(CH$_2$)$_n$]$_p$—(CH—ONO$_2$)$_q$—CH$_2$—ONO$_2$
A2): —(CH$_2$)$_2$—NH—(C=O)—(CH$_2$)$_m$—[O—(CH$_2$)$_n$]$_p$—(CH—ONO$_2$)$_q$—CH$_2$—ONO$_2$
A3): —(CH$_2$)$_m$—[O—(CH$_2$)$_n$]$_p$—(CH—ONO$_2$)$_q$—CH$_2$—ONO$_2$
wherein
R$^1$ is —H or —CH$_3$,
p is 1 or 0,
q is 1 or 0,
m is an integer ranging from 1 to 10;
n is an integer ranging from 1 to 6.

2. A compound of formula (I) according to claim 1, wherein Ra is selected from
A1): —(CHR$^1$)—NH—(C=O)—(CH$_2$)$_m$—[O—(CH$_2$)$_n$]$_p$—(CH—ONO$_2$)$_q$—CH$_2$—ONO$_2$, and
A3): —(CH$_2$)$_m$—[O—(CH$_2$)$_n$]$_p$—(CH—ONO$_2$)$_q$—CH$_2$—ONO$_2$.

3. A compound of formula (I) according to claim 2, wherein R is —CH(CH$_3$)$_2$ and
Ra is A1): —(CHR$^1$)—NH—(C=O)—(CH$_2$)$_m$—[O—(CH$_2$)$_n$]$_p$—(CH—ONO$_2$)$_q$—CH$_2$—ONO$_2$
wherein
R$^1$ is —H or —CH$_3$,
p is 1 or 0,
q is 1 or 0,
m is an integer ranging from 1 to 10;
n is an integer ranging from 1 to 6.

4. A compound of formula (I) according to claim 3, wherein Ra is selected from the group consisting of:

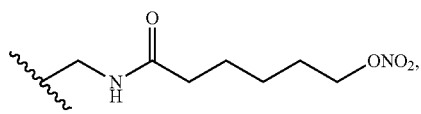
(1-A1)

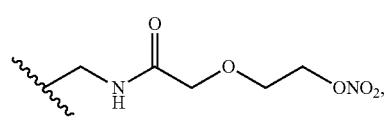
(2-A1)

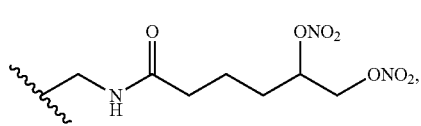
(3-A1)

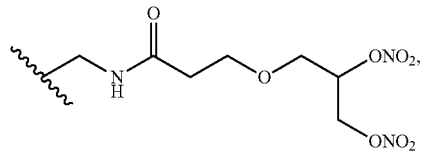
(4-A1)

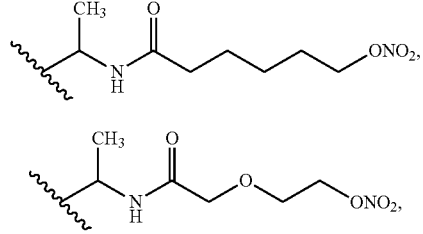
(5-A1)

(6-A1)

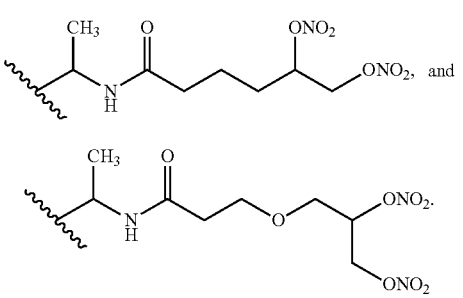
(7-A1)

(8-A1)

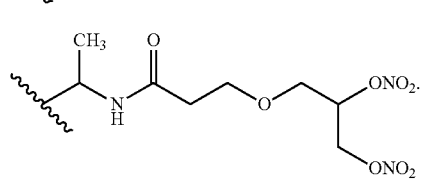

5. A compound of formula (I) according to claim 2, wherein R is —CH(CH$_3$)$_2$ and
Ra is A3): —(CH$_2$)$_m$—[O—(CH$_2$)$_n$]$_p$—(CH—ONO$_2$)$_q$—CH$_2$—ONO$_2$
wherein
p is 1 or 0,
q is 1 or 0,
m is an integer ranging from 1 to 10;
n is an integer ranging from 1 to 6.

6. A compound of formula (I) according to claim 5, wherein Ra is selected from the group consisting of:

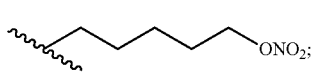
(1-A3)

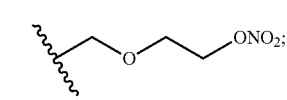
(2-A3)

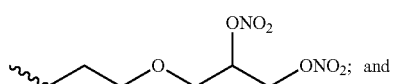
(3-A3)

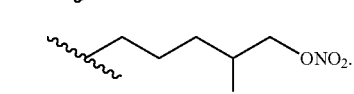
(4-A3)

7. A compound of formula (I) according to claim 1, wherein R is —H.

8. A compound of formula (I) according to claim 2 selected from the group consisting of:

(Z)-isopropyl 7-((1R,2R,3R,5S)-3,5-dihydroxy-2-((R,E)-3-(2-(6-(nitrooxy) hexanamido) acetoxy)-4-(3-(trifluoromethyl)phenoxy)but-1-enyl)cyclopentyl)hept-5-enoate (Compound (5));

(Z)-isopropyl 7-((1R,2R,3R,5S)-2-((3R,E)-3-(2-(5,6-bis(nitrooxy)hexanamido)acetoxy)-4-(3-(trifluoromethyl)phenoxy)but-1-enyl)-3,5-dihydroxycyclopentyl) hept-5-enoate (Compound (6));

(Z)-isopropyl 7-((1R,2R,3R,5S)-3,5-dihydroxy-2-((R,E)-3-(2-(2-(2-(nitrooxy)ethoxy) acetamido)acetoxy)-4-(3-(trifluoromethyl) phenoxy)but-1-enyl)cyclopentyl) hept-5-enoate (Compound (7));

(Z)-isopropyl 7-((1R,2R,3R,5S)-2-((3R, E)-3-(2-(3-(2,3-bis(nitrooxy)propoxy) propanamido)acetoxy)-4-(3-(trifluoromethyl)phenoxy)but-1-enyl)-3,5-dihydroxycyclopentyl)hept-5-enoate (Compound (8));

(Z)-isopropyl 7-((1R,2R,3R,5S)-3,5-dihydroxy-2-((R,E)-3-(6-(nitrooxy)hexanoyloxy)-4-(3-(trifluoromethyl) phenoxy)but-1-enyl)cyclopentyl)hept-5-enoate (Compound (9));

(Z)-isopropyl 7-((1R,2R,3R,5S)-2-((3R, E)-3-(5,6-bis(nitrooxy)hexanoyloxy)-4-(3-(trifluoromethyl)phenoxy)but-1-enyl)-3,5-dihydroxycyclopentyl)hept-5-enoate (Compound (10));

(Z)-isopropyl 7-((1R,2R,3R,5S)-3,5-dihydroxy-2-((R,E)-3-(2-(2-(nitrooxy)ethoxy) acetoxy)-4-(3-(trifluoromethyl)phenoxy)but-1-enyl)cyclopentyl)hept-5-enoate (Compound (11));

(Z)-isopropyl 7-((1R,2R,3R,5S)-2-((3R, E)-3-(3-(2,3-bis(nitrooxy)propoxy) propanoyloxy)-4-(3-(trifluoromethyl)phenoxy) but-1-enyl)-3,5-dihydroxycyclopentyl)hept-5-enoate (Compound (12)); and (Z)-7-((1R,2R,3R,5S)-2-((R,E)-3-(5,6-bis(nitrooxy) hexanoyloxy)-4-(3-(trifluoromethyl) phenoxy)but-1-enyl)-3,5-dihydroxycyclopentyl) hept-5-enoic acid (Compound (13)).

9. A compound of formula (I) according to claim 1, wherein R is —CH(CH$_3$)$_2$ and
Ra is A2): —(CH$_2$)$_2$—NH—(C=O)—(CH$_2$)$_m$—[O—(CH$_2$)$_n$]$_p$—(CH—ONO$_2$)$_q$—CH$_2$—ONO$_2$
wherein
p is 1 or 0,
q is 1 or 0,
m is an integer ranging from 1 to 10;
n is an integer ranging from 1 to 6.

10. A compound of formula (I) according to claim 9, wherein Ra is selected from the group consisting of:

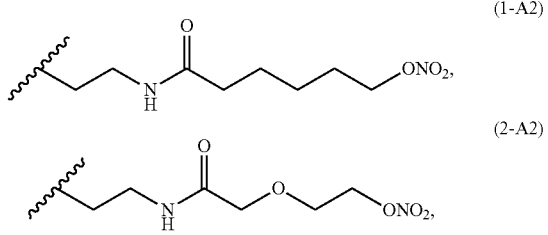

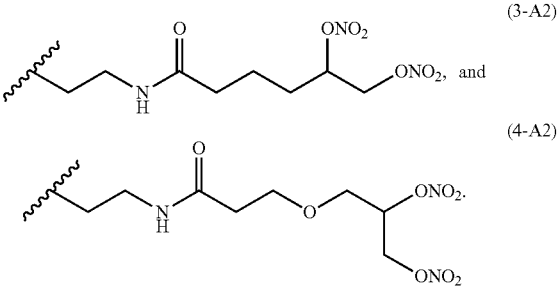

11. A compound of formula (I) according to claim 2, wherein R is —H.

12. A compound of formula (I) according to claim 9 selected from the group consisting of:

(Z)-isopropyl 7-((1R,2R,3R,5S)-3,5-dihydroxy-2-((R,E)-3-(3-(6-(nitrooxy) hexanamido) propanoyloxy)-4-(3-(trifluoromethyl)phenoxy) but-1-enyl)cyclopentyl) hept-5-enoate (Compound (1));

(Z)-isopropyl 7-((1R,2R,3R,5S)-2-((3R, E)-3-(3-(5,6-bis(nitrooxy) hexanamido) propanoyloxy)-4-(3-(trifluoromethyl)phenoxy) but-1-enyl)-3,5-dihydroxycyclopentyl) hept-5-enoate (Compound (2));

(Z)-isopropyl 7-((1R,2R,3R,5S)-3,5-dihydroxy-2-((R,E)-3-(3-(2-(2-(nitrooxy) ethoxy) acetamido) propanoyloxy)-4-(3-(trifluoromethyl)phenoxy)but-1-enyl)cyclopentyl)hept-5-enoate (Compound (3)); and (Z)-isopropyl 7-((1R,2R,3R,5S)-2-((3R, E)-3-(3-(3-(2,3-bis(nitrooxy)propoxy) propanamido)propanoyloxy)-4-(3-(trifluoromethyl) phenoxy)but-1-enyl)-3,5-dihydroxycyclopentyl)hept-5-enoate (Compound (4)).

13. A method for treating ocular hypertension, the method comprising administering to a subject in need thereof the compound of formula (I) according to claim 1.

14. A method for treating glaucoma, the method comprising administering to a subject in need thereof the compound of formula (I) according to claim 1.

15. The method according to claim 13, wherein glaucoma is primary open angle glaucoma, normal intraocular tension glaucoma, pseudoexfoliation glaucoma, acute angle-closure glaucoma or chronic closed angle glaucoma.

16. A topical ocular pharmaceutical composition comprising a compound of formula (I) according to claim 1 as active principle and a pharmaceutically acceptable excipient or a combination of excipients.

17. A composition comprising a compound of formula (I) according to claim 1 and at least another active agent selected from the group consisting of: carteolol, levobunolol, metipranolol, timolol hemihydrate, epinephrine borate, epinephrine hydrochloride, dipivefrin, apraclonidine, acetazolamide, dichlorphenamide, methazolamide, brinzolamide, dorzolamide, carbachol, pilocarpine hydrochloride, pilocarbine nitrate, pilocarpine, demecarium, echothiophate, physostigmine, and combinations thereof.

18. A method for treating ocular hypertension or glaucoma, the method comprising administering to a subject in need thereof the composition according to claim 17.

* * * * *